United States Patent
Goetz et al.

(10) Patent No.: US 9,855,405 B2
(45) Date of Patent: Jan. 2, 2018

(54) BURR HOLE CAP ASSEMBLY WITH THERAPY DELIVERY MEMBER ORIENTATION FEATURE

(75) Inventors: Steven M. Goetz, North Oaks, MN (US); Mark J. Holle, Shoreview, MN (US); Ashish Singal, Blaine, MN (US); Spencer M. Bondhus, Columbia Heights, MN (US)

(73) Assignee: Medtronic, Inc., Minneapolis, MN (US)

( * ) Notice: Subject to any disclaimer, the term of this patent is extended or adjusted under 35 U.S.C. 154(b) by 101 days.

(21) Appl. No.: 13/451,133

(22) Filed: Apr. 19, 2012

(65) Prior Publication Data
US 2012/0277670 A1 Nov. 1, 2012

Related U.S. Application Data

(60) Provisional application No. 61/480,851, filed on Apr. 29, 2011.

(51) Int. Cl.
| | | |
|---|---|---|
| A61M 25/00 | (2006.01) | |
| A61M 25/02 | (2006.01) | |
| A61N 1/05 | (2006.01) | |
| A61N 1/372 | (2006.01) | |

(52) U.S. Cl.
CPC .......... *A61M 25/02* (2013.01); *A61N 1/0539* (2013.01); *A61N 1/37223* (2013.01); *A61N 1/37252* (2013.01); *A61M 2025/0008* (2013.01); *A61M 2025/0042* (2013.01); *A61M 2025/028* (2013.01); *A61M 2025/0213* (2013.01); *A61M 2210/0687* (2013.01)

(58) Field of Classification Search
CPC ......... A61B 2019/208; A61M 25/0105; A61N 1/0539
USPC ............. 128/207; 285/239; 604/164.01, 174, 604/175, 178, 288.02, 415, 48, 506, 516, 604/533, 535, 65.8; 606/129, 130; 607/115, 116, 139
See application file for complete search history.

(56) References Cited

U.S. PATENT DOCUMENTS

| | | | | |
|---|---|---|---|---|
| 3,073,310 | A * | 1/1963 | Mocarski | 606/130 |
| 4,265,252 | A * | 5/1981 | Chubbuck et al. | 600/561 |
| 4,723,544 | A * | 2/1988 | Moore et al. | 606/130 |
| 4,955,891 | A * | 9/1990 | Carol | 606/130 |
| 4,998,938 | A * | 3/1991 | Ghajar et al. | 606/130 |
| 5,050,605 | A * | 9/1991 | Eydelman et al. | 600/422 |
| 5,056,523 | A * | 10/1991 | Hotchkiss et al. | 600/427 |
| 5,176,689 | A * | 1/1993 | Hardy | A61N 5/1031 378/206 |
| 5,203,777 | A | 4/1993 | Lee | |
| 5,279,309 | A * | 1/1994 | Taylor et al. | 600/595 |
| 5,515,160 | A * | 5/1996 | Schulz et al. | 356/241.1 |
| 5,572,999 | A * | 11/1996 | Funda et al. | 600/118 |

(Continued)

*Primary Examiner* — Scott Medway
(74) *Attorney, Agent, or Firm* — Shumaker & Sieffert, P.A.

(57) ABSTRACT

In some examples, a burr hole cap assembly includes one or more markers that indicate a rotational orientation of a therapy delivery member relative to the burr hole cap assembly, where the therapy delivery member extends through an opening defined by the burr hole cap assembly. In addition, in some examples, the burr hole cap assembly includes a feature that indicates the rotational orientation of the therapy delivery member after the therapy delivery member is implanted in the patient. The feature can include the one or more markers in some examples.

36 Claims, 9 Drawing Sheets

(56) References Cited

U.S. PATENT DOCUMENTS

| | | | |
|---|---|---|---|
| 5,588,430 A * | 12/1996 | Bova | A61B 6/035 |
| | | | 378/204 |
| 5,695,501 A * | 12/1997 | Carol et al. | 606/130 |
| 5,927,277 A * | 7/1999 | Baudino et al. | 600/386 |
| 5,989,230 A * | 11/1999 | Frassica | 604/264 |
| 6,152,933 A * | 11/2000 | Werp | A61M 27/006 |
| | | | 604/165.01 |
| 6,267,769 B1 * | 7/2001 | Truwit | 606/130 |
| 6,272,370 B1 * | 8/2001 | Gillies et al. | 600/411 |
| 6,282,437 B1 * | 8/2001 | Franck et al. | 600/429 |
| 6,356,792 B1 * | 3/2002 | Errico et al. | 607/116 |
| 6,419,680 B1 * | 7/2002 | Cosman et al. | 606/130 |
| 6,491,699 B1 * | 12/2002 | Henderson et al. | 606/130 |
| 6,572,624 B2 * | 6/2003 | U et al. | 606/130 |
| 6,689,142 B1 * | 2/2004 | Tremaglio et al. | 606/130 |
| 6,752,812 B1 * | 6/2004 | Truwit | 606/130 |
| 7,004,948 B1 * | 2/2006 | Pianca et al. | 606/129 |
| 7,235,084 B2 * | 6/2007 | Skakoon et al. | 606/130 |
| 7,479,146 B2 * | 1/2009 | Malinowski | 606/130 |
| 7,497,863 B2 * | 3/2009 | Solar et al. | 606/130 |
| 7,636,596 B2 * | 12/2009 | Solar | 600/429 |
| 7,637,915 B2 * | 12/2009 | Parmer et al. | 606/108 |
| 7,840,253 B2 * | 11/2010 | Tremblay et al. | 600/424 |
| 8,029,482 B2 * | 10/2011 | Maniar et al. | 604/288.02 |
| 8,257,325 B2 * | 9/2012 | Schweikert et al. | 604/288.01 |
| 8,644,907 B2 * | 2/2014 | Hartmann et al. | 600/424 |
| 2002/0019641 A1 * | 2/2002 | Truwit | 606/130 |
| 2002/0082612 A1 * | 6/2002 | Moll et al. | 606/130 |
| 2003/0199886 A1 * | 10/2003 | Thomas | 606/130 |
| 2004/0052333 A1 * | 3/2004 | Sayre | A61B 90/39 |
| | | | 378/163 |
| 2005/0075681 A1 * | 4/2005 | Rezai et al. | 607/48 |
| 2007/0078391 A1 * | 4/2007 | Wortley et al. | 604/116 |
| 2007/0233156 A1 * | 10/2007 | Metzger | A61B 17/155 |
| | | | 606/130 |
| 2008/0009746 A1 * | 1/2008 | Forster et al. | 600/467 |
| 2008/0255629 A1 * | 10/2008 | Jenson et al. | 607/19 |
| 2008/0269740 A1 | 10/2008 | Bonde et al. | |
| 2009/0204192 A1 | 8/2009 | Carlton | |
| 2011/0105910 A1 * | 5/2011 | Lawson et al. | 600/474 |
| 2011/0166442 A1 * | 7/2011 | Sarvazyan | 600/424 |
| 2012/0197368 A1 * | 8/2012 | Reisinger | A61N 1/3754 |
| | | | 607/116 |
| 2013/0072943 A1 * | 3/2013 | Parmar | 606/130 |
| 2013/0096570 A1 * | 4/2013 | Solar | A61B 90/11 |
| | | | 606/108 |
| 2014/0275991 A1 * | 9/2014 | Potter et al. | 600/424 |

* cited by examiner

BURR HOLE CAP ASSEMBLY WITH THERAPY DELIVERY MEMBER ORIENTATION FEATURE

This application claims the benefit of U.S. Provisional Patent Application Ser. No. 61/480,851 by Goetz et al., which was filed on Apr. 29, 2011, and is entitled "BURR HOLE CAP ASSEMBLY WITH THERAPY DELIVERY MEMBER ORIENTATION FEATURE." U.S. Provisional Application Ser. No. 61/480,851 by Goetz et al. is incorporated herein by reference in its entirety

TECHNICAL FIELD

The disclosure relates to burr hole cap assemblies.

BACKGROUND

In some medical systems, a therapy delivery member (e.g., a lead or a catheter) is implanted in a brain of a patient. The therapy delivery member may access regions of the brain through a burr hole formed through the patient's skull. A burr hole cap assembly, which is positioned within the burr hole, may be used to retain the position of the therapy delivery member relative to the burr hole, as well as substantially plug the burr hole.

SUMMARY

In general, the disclosure is directed to a burr hole cap assembly that indicates a rotational orientation of a therapy delivery member relative to the burr hole cap assembly, where the therapy delivery member extends through a base of the burr hole cap assembly. The burr hole cap assembly includes one or more features that indicate the rotational orientation of the therapy delivery member relative to the burr hole cap assembly. In some examples, the feature is a marker that indicates the rotational orientation of the therapy delivery member. In some examples, the marker is visible by the clinician, without the use of any additional visualization tools (e.g., a medical imaging device), at the time the therapy delivery member is implanted in the patient. In addition, in some examples, the marker is movable relative to a part of the burr hole cap assembly, and a clinician may manipulate the marker at the time the therapy delivery member is implanted in the patient so that the marker indicates the rotational orientation of the therapy delivery member relative to the burr hole cap assembly.

In some examples, the burr hole cap assembly includes a feature that indicates the rotational orientation of the therapy delivery member after the therapy delivery member is implanted in the brain of the patient. For example, the burr hole cap assembly may include a reactive element (e.g., an inductor in a circuit with a resistor and/or a capacitive element, or a capacitive element in a circuit) that has an characteristic (e.g., an impedance, such as an inductive reactance of the inductor, or a capacitance) that is indicative of the rotational orientation of the therapy delivery member relative to the burr hole cap assembly.

In one aspect, the disclosure is directed to a system comprising a base that is configured to fit inside of a burr hole in a cranium of a patient, where the base defines an opening that is configured to receive a therapy delivery member, a marker that is configured to indicate a rotational orientation of the therapy delivery member relative to the base, and a cover that is configured to substantially cover the opening defined by the base.

In another aspect, the disclosure is directed to a method comprising introducing a therapy delivery member through an opening defined by a base, where the base is configured to fit inside of a burr hole in a cranium of a patient, and indicating a rotational orientation of the therapy delivery member relative to the base with a marker.

In another aspect, the disclosure is directed to a system comprising means for covering a burr hole in a cranium of a patient, wherein the means for covering the burr hole defines an opening configured to receive a therapy delivery member, and means for indicating a rotational orientation of the therapy delivery member relative to the means for covering the burr hole.

In another aspect, the disclosure is directed to a method comprising identifying a marker of a burr hole cap assembly, where the burr hole cap assembly comprises a base that is configured to fit inside of a burr hole in a cranium of a patient, where the base defines an opening that is configured to receive a therapy delivery member, and determining a rotational orientation of a therapy delivery member relative to the base based on a position of the marker relative to the base.

In another aspect, the disclosure is directed to a method comprising determining a characteristic of a reactive element that changes based on a position of a marker of a burr hole cap assembly relative to a base of the burr hole cap assembly, wherein the base is configured to fit inside of a burr hole in a cranium of a patient and defines an opening that is configured to receive a therapy delivery member, and, with a processor, determining a rotational orientation of the therapy delivery member relative to the base based on the characteristic of the reactive element.

In another aspect, the disclosure is directed to an article of manufacture comprising a computer-readable storage medium. The computer-readable storage medium comprises computer-readable instructions for execution by a processor. The instructions cause a programmable processor to perform any part of the techniques described herein. The instructions may be, for example, software instructions, such as those used to define a software or computer program. The computer-readable medium may be a computer-readable storage medium such as a storage device (e.g., a disk drive, or an optical drive), memory (e.g., a Flash memory, read only memory (ROM), or random access memory (RAM)) or any other type of volatile or non-volatile memory that stores instructions (e.g., in the form of a computer program or other executable) to cause a programmable processor to perform the techniques described herein. The computer-readable medium may be nontransitory.

The details of one or more examples are set forth in the accompanying drawings and the description below. Other features, objects, and advantages will be apparent from the description and drawings, and from the claims.

DETAILED DESCRIPTION

Figure 1:
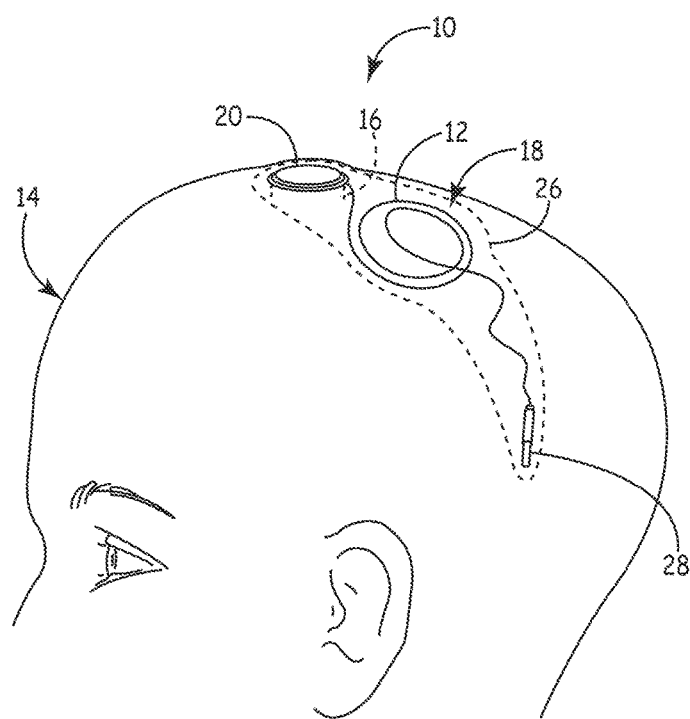
FIG. 1 is a conceptual illustration of a therapy delivery member implanted in a brain of a patient through a burr hole defined through a cranium of the patient.

FIG. 1 is a conceptual illustration of a part of an implanted therapy system 10, which includes therapy delivery member 12 implanted within patient 14 through burr hole 16 defined through cranium 18 of patient 14. Therapy system 10 further includes burr hole cap assembly 20, which is configured to substantially fix therapy delivery member 12 in place relative to burr hole 16 in cranium 18, as well as substantially cover burr hole 16. Securing a portion of therapy delivery member 12 that passes through cranium 18 may help secure a portion (e.g., a distal portion) of therapy delivery member 12 that is configured to deliver therapy to a target tissue site in the brain of patient 14. As described in further detail below, burr hole cap assembly 20 includes one or more features that indicate a rotational orientation of therapy delivery member 12 relative to burr hole cap assembly 20.

The rotational orientation of therapy delivery member 12 relative to burr hole cap assembly 20 may be useful for various purposes, such as for programming a medical device (implantable or external) that delivers therapy to patient 14 via therapy delivery member 12. In addition, in some examples, the rotational orientation of therapy delivery member 12 relative to burr hole cap assembly 20 may be useful for interpreting one or more physiological signals sensed by sensing electrodes of therapy delivery member 12 because the rotational orientation of therapy delivery member 12 relative to burr hole cap assembly 20 may indicate the orientation of the sensing electrodes relative to one or more brain structures of patient 14 (e.g., when the orientation of burr hole cap assembly 20 relative to the one or more brain structures may be known).

Therapy delivery member 12 can be any suitable medical member that is configured to deliver therapy to one or more target tissue sites within patient 14, e.g., from a medical device to the one or more target tissue sites, or to sense one or more physiological parameters of patient 14. Therapy delivery member 12 is relatively torsionally stiff, such that therapy delivery member 12 does not significantly rotate between the point at which therapy delivery member 12 extends from burr hole cap assembly 20 and one or more therapy delivery elements (e.g., sensing and/or stimulation electrodes, and/or one or more fluid delivery ports) of therapy delivery member 12. In this way, the rotational orientation of therapy delivery member 12 relative to burr hole cap assembly 20, determined from the portion of therapy delivery member 12 extending from burr hole cap assembly 20, may indicate the rotational orientation of one or more therapy delivery elements of therapy delivery member 12.

Although not shown in FIG. 1, therapy delivery member 12 may be connected to a medical device either directly or indirectly (e.g., via one or more extension elements). The medical device may be implanted or may be carried external to patient 14. In some examples, therapy delivery member 12 is a medical lead that carries a set of electrodes near a distal end, where the electrodes may be configured to deliver electrical stimulation therapy from the medical device to tissue proximate the electrodes. Instead of or in addition to a medical lead, therapy delivery member 12 may be a catheter that defines one or more delivery ports that may be used to deliver a therapeutic agent (e.g., a pharmaceutical agent) from a medical device to one or more target tissue sites within patient 14.

In the example therapy system 10 shown in FIG. 1, therapy delivery member 12 forms a strain relief loop in subgaleal pocket 26, which is under the scalp of patient 14. Subgaleal pocket 26 may have any suitable dimensions, such as an approximately 50 millimeters (mm) diameter, and may be formed using any suitable technique, such as blunt dissection. In other examples, therapy delivery member 12 may not form a strain relief loop or may form a strain relief loop in another suitable region in patient 14. In the example shown in FIG. 1, therapy delivery member 12 includes cap 28, which can be delivered (e.g., via tunneling through tissue) to another region in patient 14, such as the region in which a medical device is implanted in patient 14. The medical device may be implanted outside of cranium 18 (e.g., in a chest region of patient 14) in some examples. However, in some examples, the medical device may be implanted in cranium 18 of patient 14, and, as a result, there may be less strain relief of therapy delivery member 12, or distance in which therapy delivery member 12 is tunneled to the cranially implanted medical device compared to examples in which the medical device implanted in a portion of the body of patient 14 outside the cranium 118.

As noted above, knowledge of a relative rotational orientation between therapy delivery member 12 and one or more brain structures may be useful for programming therapy delivery by a medical device, such as for selecting the one or more electrodes that are used to deliver electrical stimulation to patient 14 in examples in which therapy delivery member 12 comprises a lead or determining the appropriate bolus size or rate of delivery for a therapeutic agent that may provide therapeutic results for patient 114. In addition, in some examples, knowledge of the relative rotational orientation between therapy delivery member 12 and burr hole cap assembly 20 may be useful for positioning therapy delivery member 12 in patient 14 at a desired orientation relative to one or more brain structures. Knowledge of the relative rotational orientation between therapy delivery member 12 and burr hole cap assembly 20 may be particularly useful if therapy delivery elements of therapy delivery member 12 are symmetrical (relative to a longitudinal axis of member 12) or unsymmetrical (e.g., a catheter with more ports on one side than another or a lead with electrodes that are designed to provide higher resolution through some angles than others).

Burr hole cap assembly 20 includes one or more features that indicate the relative rotational orientation between therapy delivery member 12 extending through burr hole 16 and burr hole cap assembly 20. The relative rotational orientation between therapy delivery member 12 and burr hole cap assembly 20 may indicate, for example, the orientation of electrodes, a fluid delivery port, or other therapy delivery features of therapy delivery member 12 relative to one or more brain structures of patient 14. The relative orientation between burr hole cap assembly 20 and one or more brain structures may be known, e.g., based on the stereotactic or other surgical data used to define burr hole 16, in which burr hole cap assembly 20 is placed. Thus, the relative orientation of therapy delivery member 12 relative to the one or more brain structures can be determined based on the relative orientation of therapy delivery member 12 and burr hole cap assembly 20.

As described in further detail below with respect to FIGS. 5-14, in some examples, burr hole cap assembly 20 includes one or more markers that can be aligned with a corresponding marker on therapy delivery member 12. In this way, the one or more markers of burr hole cap assembly 20 may indicate the relative rotational orientation of therapy delivery member 12. In some examples, the one or more markers are in fixed positions relative to burr hole cap assembly 20, while in other examples, the one or more markers are movable relative to burr hole cap assembly 20.

In some examples, the location of the one or more markers of burr hole cap assembly 20 may be determined after therapy delivery member 12 is implanted in patient 14 and, e.g., after burr hole cap assembly 20 is covered by the patient's scalp or otherwise not readily visible by the clinician without the aid of visualization tools. For example, the one or more markers may be radiopaque and visible via medical imaging (e.g., x-ray or computed tomography (CT)). As another example, in addition to or instead of the radiopaque marker, in some examples, the one or more markers of burr hole cap assembly may protrude from cranium 18 of patient 14, such that a clinician may locate the markers through the patient's skin by a clinician via palpation. In addition to or instead of the aforementioned markers, burr hole cap assembly 20 may include a reactive element (e.g., an inductor in a circuit that includes a capacitor and/or a resistor or combinations thereof) whose impedance (e.g., an inductive reactance of the inductor) changes as a function of the position of a marker of burr hole cap assembly 20. An external device may energize the reactive element and determine the rotational position of the marker of burr hole cap assembly 20, and, therefore, the rotational position of a marker on therapy delivery member 12, based on the impedance of the reactive element.

With existing systems, a clinician may implant a therapy delivery member in patient 14 through burr hole 16 and subsequently determine and record a rotational orientation of the therapy delivery member in an idiosyncratic manner. For example, if therapy delivery member 12 includes one or more segmented or partial electrodes that extend around less than the entire outer perimeter of element 12, the clinician may determine which direction (e.g., relative to an anatomical landmark) a particular electrode was facing when therapy delivery member 12 was implanted in patient 14. The clinician may then manually record this information in a written record or in an electronic device (e.g., a medical device programmer or another computing device). The written record or electronic device containing the orientation information may or may not remain with patient 14, which may reduce the availability of the information to clinicians that treat patient 14.

Moreover, reliance on the implanting clinician to provide the information indicating the rotational orientation of an implanted therapy delivery member may result in different approaches for conveying the information between clinicians. For example, one clinician may indicate a therapy delivery member is oriented at 30 degrees (°) relative to a particular point on a burr hole cap assembly or an anatomical landmark, while another clinician may refer to this exact same orientation as −30°.

In contrast to these existing systems, with therapy system 10, information indicating a relative rotational orientation of therapy delivery member 12, e.g., relative to burr hole cap assembly 20 and/or one or more brain structures, remains with patient 14, and at a known place, e.g., near burr hole 16, which is the point of implant of therapy delivery member 12 in patient 14. In this way, information indicative of the rotational orientation of the therapy delivery member relative to burr hole cap assembly 20 is built into features provided by burr hole cap assembly 20. Thus, in some examples, burr hole cap assembly 20 may relieve the burden on a clinician to accurately communicate and/or record the orientation of the therapy delivery member as implanted in patient 14, as well as communicate and record the information in a manner that is expected to be understood by other clinicians. In addition, burr hole cap assembly 20 may standardize how such information is provided across multiple clinicians. Multiple clinicians using burr hole cap assembly 20 may indicate the rotational orientation of therapy delivery member 12 in a consistent way.

While a clinician can attempt to implant therapy delivery member 12 so that it has a particular rotational orientation relative to burr hole cap assembly 20, in some cases, the clinician may find this burdensome and difficult to achieve. In some cases, burr hole cap assembly 20 enables the clinician to implant therapy delivery member 12 without trying to maintain a specific rotational orientation between therapy delivery member 12 and burr hole cap assembly 20. This may be advantageous because requiring changes to surgical procedures may cause the procedure to take longer. After implantation of therapy delivery member 12 in patient 14, the clinician may determine the relative rotational orientation between therapy delivery member 12 and burr hole cap assembly 20. In some cases, this may be done at the time of implant, while in other examples, this may be done some time after implant, e.g., after burr hole cap assembly 20 is covered up with the skin of patient 14.

Burr hole cap assembly 20 may provide a convenient mechanism by which the clinician may record information that indicates the rotational orientation of therapy delivery member 12 relative to burr hole cap assembly 20. In some examples, the clinician may determine the rotational orientation of therapy delivery member 12 relative to burr hole cap assembly 20 at the time therapy delivery member 12 is implanted in patient 14, which may be the time at which information about the rotational orientation is readily accessible to the clinician. For example, at the time therapy delivery member 12 is implanted in patient 14, the clinician may visually ascertain, without the aid of any imaging devices, the rotational orientation of therapy delivery member 12 relative to burr hole cap assembly 20.

In some examples, burr hole cap assembly 20 is configured to transmit information indicative of the relative rotational orientation between therapy delivery member 12 and burr hole cap assembly 20 to an external device, such as a medical device programmer or a reader device (described below with respect to FIG. 12). In addition, in some examples, burr hole cap assembly 20 may enable a clinician to determine the relative orientation of therapy delivery member 12 and the brain structures of patient 14 without medical imaging. Medical imaging may be inconvenient, costly, or both, in some cases.

Even if therapy delivery member 12 includes a radiopaque marker, the radiopaque marker on member 12 by itself may not be useful for determining the direction the one or more therapy delivery elements of therapy delivery member 12 face within patient 14. For example, the marker of therapy delivery member 12 may be covered by burr hole cap base 20, which may complicate the imaging of the marker. Placement of a marker on burr hole cap assembly 20 may be advantageous in that the marker may be more visible to a clinician (e.g., via medical imaging) compared to a marker on therapy delivery member 12. In addition, due to the placement of burr hole cap assembly 20 in patient 14 versus the placement of an implanted therapy delivery member 12 in patient 14, the radiopaque marker on burr hole cap assembly 20 may allow for a simpler or more available form of medical imaging (e.g., x-ray or fluoroscopy) to determine the location of the radiopaque marker compared to the forms of medical imaging (e.g., magnetic resonance imaging (MRI) or computed tomography imaging) that may be required to determine the location of the marker on therapy delivery element 12.

In addition or instead, imaging of a marker on therapy delivery member 12 by itself may not be useful for determining which direction the one or more therapy delivery elements of therapy delivery member 12 face in patient 114. For example, an x-ray image may not provide a reference point for the marker of therapy delivery member 12, such that an image of the marker itself may not provide any information regarding directionality of the one or more therapy delivery elements of therapy delivery member 12. On the other hand, due to the position of burr hole cap assembly 20 on cranium 18 of patient 14, a reference point for an imaged marker of burr hole cap assembly 20 may be automatically known. As an example, based on an image of a marker of burr hole cap assembly 20, a clinician may approximate where the marker is on cranium 18, which may then indicate which direction the one or more therapy delivery elements of therapy delivery member 12 are facing relative to burr hole cap assembly 20.

Figure 2:
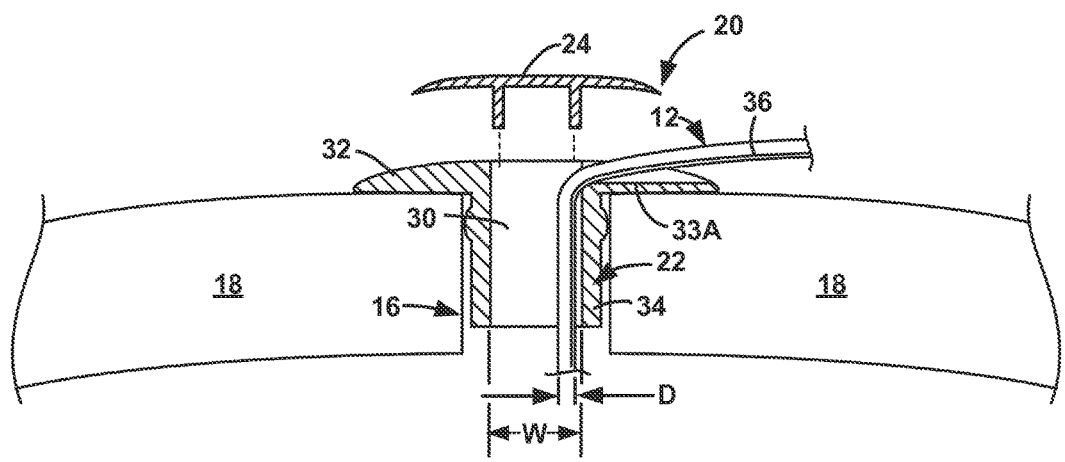
FIG. 2 is a conceptual cross-sectional illustration of a therapy delivery member extending through a base of a burr hole cap assembly that is inserted in a burr hole defined through a cranium of a patient.

FIG. 2 is a schematic cross-sectional illustration of therapy delivery member 12 extending through base 22 of burr hole cap assembly 20, where base 22 is positioned within burr hole 16 through cranium 18 of patient 14. The cross-section is taken through burr hole cap assembly 20, as well as through a center of therapy delivery member 12. As shown in FIG. 2, burr hole cap assembly 20 includes base 22, which defines opening 30, and cover 24 which is shown in FIG. 2 in a disassembled state, in which cover 24 is not mechanically coupled to base 22. Assembly lines are shown in FIG. 2 to illustrate how cover 24 may be aligned with base 22 such that it partially fits within opening 30 define by base 22 and substantially covers opening 30.

Opening 30 defined by base 22 is configured to receive therapy delivery member 12. In some examples, opening 30 has a circular cross-section, but other cross-sectional shapes (e.g., quadrilateral) are contemplated. In the example shown in FIG. 2, opening 30 has a width W (e.g., width may be a diameter in the case of an opening with a circular cross-section), which is the width at the widest portion of opening 30. In addition, opening 30 is sized to receive therapy delivery member 12. For example, width W may be greater than a greatest dimension of therapy delivery member 12 in a direction that is substantially perpendicular to a longitudinal axis of therapy delivery member 12. For example, in FIG. 2, width W of opening 30 is sized to be larger than a diameter D of therapy delivery member 12 in examples in which therapy delivery member 12 has a circular cross-section. In one example, for example, width W of opening 30 is about 14 mm and diameter D of therapy delivery member 12 is about 1.3 mm. Other dimensions are contemplated.

Base 22 is configured to be inserted in burr hole 16 and may help protect edges of burr hole 16. Base 22 may have any suitable configuration. In the example shown in FIG. 2, base 22 includes flange 32 that radially extends from shaft 34. Flange 32 may be integrally formed with shaft 34, or may be physically separate from shaft 34 and mechanically coupled to shaft 34. Flange 32 is configured to engage with cranium 18 outside of burr hole 16 and shaft 34 is configured to engage with cranium 18 within burr hole 16. The intersection between flange 32 and shaft 34 may cover the edges of burr hole 116. The extension of flange 32 in a generally radially outward direction from shaft 34 helps to secure burr hole cap assembly 20 to an outer surface (i.e., the surface opposite the surface closest to the brain) of cranium 18.

In some examples, base 22 and cap 24 may be configured to minimize vertical height of the structure above the outer surface of cranium 18, which may help manage, minimize, and control the reossification (bone growth) of the burr hole post surgically.

In the example shown in FIG. 2, base 22 is configured such that therapy delivery member 12 extends from a side of burr hole cap assembly 20, rather than from a top of burr hole cap assembly 20 (e.g., the surface furthest from cranium 18) when burr hole cap assembly 20 is placed in burr hole 18. In one example, flange 32 defines a plurality of grooves, including groove 33A, which is configured to receive therapy delivery member 12. Therapy delivery member 12 may be configured to extend from burr hole cap assembly 20 through groove 33A. Groove 33A may be, for example, a channel configured to guide therapy delivery member 12 out of burr hole cap assembly 20. In some examples, flange 32 of base 22 defines a plurality of grooves, which may enable a clinician to select the point around base 22 that therapy delivery member 12 exits burr hole cap assembly 20. In some examples, grooves defined by flange 32 may be radially oriented or may begin radially oriented but then curve to spiral therapy deliver element 112, allowing the lead to more gradually enter into strain relief loops surrounding burr hole 16.

In other examples, burr hole cap assembly 20 is configured such that therapy delivery member 12 exits burr hole cap assembly 20 from another surface of assembly 20, such as from a top of burr hole cap assembly 20. For example, cover 24 may define an opening that substantially aligns with opening 30 in base 22 when cover 24 is connected to base 22, and therapy delivery member 12 may exit burr hole cap assembly 20 through the opening defined by cover 24. This may permit the radius of curvature of therapy delivery element 12 as it exits burr hole cap assembly 20 to be controlled, which may help maintain the integrity of therapy delivery element 12. Other techniques for guiding therapy delivery member 12 out of burr hole cap assembly 20 may be used. The techniques may be configured to guide therapy delivery member 12 in a manner that helps maintain the mechanical integrity of therapy delivery member 12.

Base 22 may be affixed to cranium 18 of patient 14 using any suitable technique, e.g., by suturing or via set screws. For example, base 22 may define apertures configured to receive one or more sutures, set screws, by mechanical interference fit, or by screwing base 22 into the burr hole itself. In some examples, at least a portion of base 22 may be formed from a compressible material, such that shaft 34 of base 22 may be sized as needed to accommodate a predetermined range of burr hole sizes. In other examples, base 22 is sized specifically for one burr hole size.

Cover 24 is configured to be mechanically connected to base 22 and substantially cover (e.g., plug) opening 30 defined by base 22. In this way, cover 24 may substantially cover burr hole 16. In some examples of burr hole cap assembly 20, cover 24 is also configured to fix therapy delivery member 12 substantially in place, e.g., in groove 33A in examples in which base 22 defines groove 33A, thereby substantially retaining the relative position between therapy delivery member 12 and burr hole 16 when burr hole cap 20 is substantially fixed to cranium 18. In the example shown in FIG. 2, cover 24 is configured to cover groove 33A (as well as the other grooves 33), such that when cover 24 is mechanically connected to base 22, therapy delivery element 12 extends from burr hole cap assembly 20 through a relatively small opening defined between base 22 and cover 24. In other examples, therapy delivery member 12 is fixed substantially in place by base 22, or both base 22 and cover 24.

In the example shown in FIG. 2, therapy delivery member 12 extends through opening 30 defined by base 22 of burr hole cap assembly 20 to access a brain of patient 14, which is positioned on the other side of cranium 18 from burr hole cover 24. When cover 24 is installed over base 22 and cover 24 is secured to base 22 (e.g., via a snap fit, an adhesive or any other suitable mechanically fixation), cover 24 helps retain the position of therapy delivery member 12 relative to burr hole 16. As previously discussed, this may help secure a portion (e.g., a distal portion) of therapy delivery member 12 that is configured to deliver therapy to one or more target tissue sites in the brain of patient 14.

Therapy delivery member 12 may be introduced into patient 14 using any suitable technique. In some examples, a distal end of therapy delivery member 12 may be guided to a target tissue site within patient 14 (e.g., within the brain of patient 14) with the aid of a stereotactic instrument, which may permit a very precise movement of member 12 within patient. In some of these examples, cover 24 is configured to fit over base 22 while therapy delivery member 12 is stilt retained by the stereotactic instrument and held in place relative to the target tissue site via the stereotactic instrument. Upon installation of cover 24 over base 22, cover 24 may substantially fix therapy delivery member 12 in place relative to burr hole 16; in examples in which therapy delivery member 12 is relatively rigid, cover 24 may also substantially fix therapy delivery member 12 at the target tissue site.

In other examples, cover 24 may be configured to fit over base 22 after therapy delivery member 12 is released from the stereotactic instrument. For example, base 22 may include one or more features that substantially fixes the position of therapy delivery member 12 relative to base 22 prior to installation of cover 24. As an example, groove 33 may be configured to hold a portion of therapy delivery member 12 retained in groove 33 by friction fit. The clinician implanting therapy delivery member 12 in patient 14 may introduce therapy delivery member 12 into groove 33 before or after release of therapy delivery member 12 from the stereotactic instrument (or other instrument used to implant therapy delivery member 12). Other techniques may also be used to substantially fix the position of therapy delivery member 12 relative to base 22 prior to installation of cover 24.

In the example shown in FIG. 2, therapy delivery member 12 comprises marker 36 that corresponds to a specific circumferential location, that is in a known position relative to a therapy delivery feature (e.g., one or more electrodes or one or more fluid delivery ports) of therapy delivery member 12. Marker 36 is in a fixed position relative to the outer perimeter of therapy delivery member 12. As described in further detail with respect to FIGS. 3A-14, marker 36 is a visual aid that can be used by a clinician to determine the relative rotational orientation between therapy delivery member 12 and burr hole cap assembly 20, e.g., after therapy delivery member 12 is implanted in patient 14.

In some examples, marker 36 is visible to the human eye without the aid of additional devices. For example, marker may include any one or more of a graphic marking on an outer surface of therapy delivery member 12, a dent in the outer surface, a tab or other structure that protrudes from the outer surface, and the like. In addition to being a marker visible to the human eye without the aid of additional devices, in some examples, marker 36 is radiopaque so that it can be viewed after therapy delivery member 12 is implanted in patient 14 and burr hole 16 and burr hole cap assembly 20 is covered up by skin.

Marker 36 may have any suitable configuration. In some examples, marker 36 is a stripe that is longer (where the length is measured along a longitudinal axis of therapy delivery member 12) than wide (where the width is measured in a direction substantially perpendicular to the longitudinal axis of member 12). In other examples, marker 36 may be circular or have an irregular shape. In the example shown in FIG. 2, marker 36 does not extend along the entire length of therapy delivery member 12. Rather, marker 36 is positioned along a portion of therapy delivery member 12 that is expected to protrude from burr hole cap assembly 20 when the one or more therapy delivery elements (e.g., electrodes or fluid delivery portions) of member 12 are positioned at one or more target tissue sites in the brain of patient 14. In other examples, marker 36 extends along the entire length of therapy delivery member 12 so that marker 36 is substantially continuously visible as therapy delivery member 12 is implanted in patient 14.

In addition, in other examples, marker 36 can be circumferentially aligned with one or more additional markers (not shown in FIG. 2). For example, marker may be positioned near a proximal end of therapy delivery member 12 while a second marker may be positioned near a distal end of therapy delivery member 12, where marker 36 and the second marker may share a circumferential position. These markers may be considered to be axially displaced from each other (e.g., displaced along a longitudinal axis of therapy delivery member 12). An example of lead with axially displaced, but circumferentially aligned axial markers is shown and described with respect to FIG. 3B.

Figure 3A:
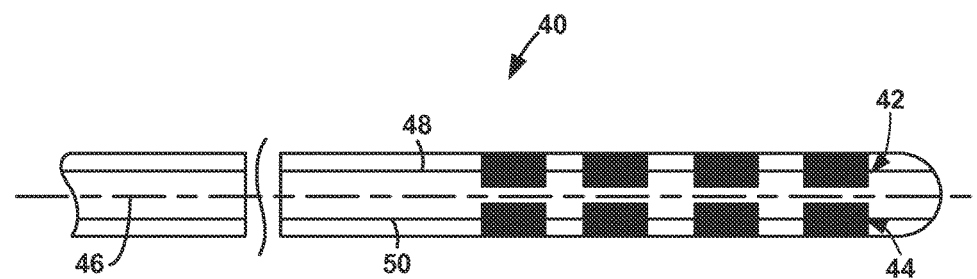
FIGS. 3A and 3B are conceptual side views of example therapy delivery members, which each includes a plurality of columns of electrodes and markers that indicate the circumferential positions of the columns of electrodes.

While one marker 36 at one circumferential position is shown in FIG. 2, in other examples, therapy delivery member 12 may include a plurality of markers that have different circumferential positions. An example of a therapy delivery member with a plurality of markers is shown in FIG. 3A. FIG. 3A is a conceptual side view of therapy delivery member 40, which includes a plurality of columns of electrodes 42, 44, where each column 42, 44 includes a plurality of electrodes separated from each other along longitudinal axis 46 of therapy delivery member 40. The electrodes in each column 42, 44 substantially share a circumferential position around the outer circumference of therapy delivery member 40. The electrodes may be used to, for example, deliver electrical stimulation therapy to tissue of patient 14 and/or sense one or more physiological parameters of patient 14. Therapy delivery member 40 may include any suitable number of columns of electrodes, such as two, three, four or more.

Therapy delivery member 40 further includes first marker 48 that is indicative of the circumferential position of one column of electrodes 42 and second marker 50 that is indicative of the circumferential position of another column of electrodes 44. In the example shown in FIG. 3B, markers 48, 50 are circumferentially aligned with the respective column of electrodes 42, 44. In some examples, markers 48, 50 are circumferentially aligned with a center line that substantially bisects the electrodes of the respective column of electrodes 42, 44, while in other examples, markers 48, 50 are circumferentially aligned with another part of the electrodes of the respective column of electrodes 42, 44, such as an edge of the electrodes.

Figure 3B:
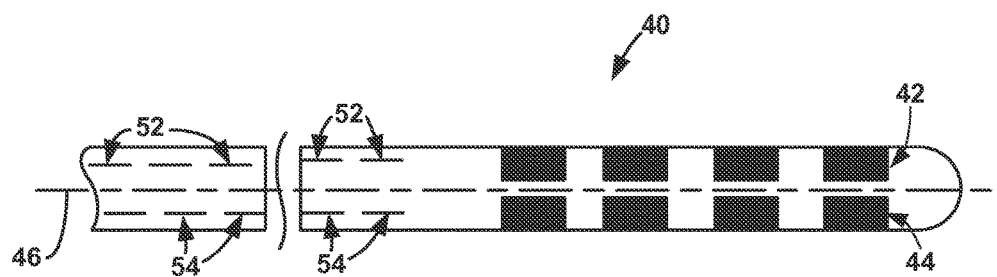

In the example shown in FIG. 3A, markers 48, 50 extend along the entire length of therapy delivery member 40. In other examples, as shown in FIG. 3B, markers of therapy delivery member 40 may not extend along the entire length of therapy delivery member 40. Markers of therapy delivery members described herein can extend along any suitable length of the therapy delivery member up to the entire length, such as about 10% to about 80% of the length of the therapy delivery member.

In FIG. 3B, rather than markers 48, therapy delivery member 40 includes a plurality of markers 52 that share a circumferential position around the outer circumference of therapy delivery member 40, and markers 54 share a circumferential position around the outer circumference of therapy delivery member 40. Adjacent markers 52 are separated from each other along longitudinal axis 46 of therapy delivery member 40, and adjacent markers 54 are separated from each other along longitudinal axis 46 of therapy delivery member 40. Markers 52, 54 are positioned along a portion of therapy delivery member 40 that may extend from burr hole 16 when columns of electrodes 42, 44 are implanted at a target stimulation site within a brain of patient 14, and therapy delivery member 40 extends through burr hole 16 (e.g., as shown in FIG. 2 with respect to therapy delivery member 12).

Figure 4:
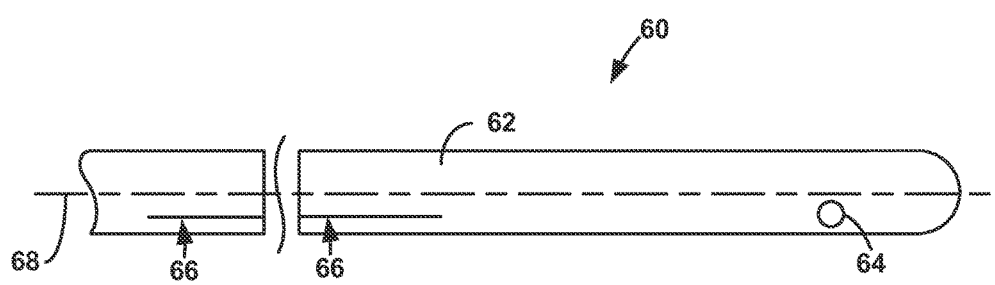
FIG. 4 is conceptual side view of an example therapy delivery member, which includes a fluid delivery port and a marker that indicate the circumferential position of the fluid delivery port.

As described above, in some examples, therapy delivery member 12 (FIGS. 1 and 2) may be configured to deliver a therapeutic agent to one or more target tissue sites in patient 14. FIG. 4 is an example of such a therapy delivery member 60, which includes body 62 including a fluid delivery conduit (not shown in FIG. 4) that terminates at a fluid delivery port 64, and a marker 66 that indicates the circumferential position of the fluid delivery port 64. In the example shown in FIG. 4, fluid delivery port 64 is on a longitudinal surface of body 62. Marker 66 may be useful for determining the rotational orientation of port 64, e.g., when port 64 is not visible to the implanting clinician. Marker is circumferentially aligned with port 64. In some examples, marker 66 is circumferentially aligned with a center of port 64, while in other examples, marker 66 is circumferentially aligned with another part of port 64, such as an edge of port 64.

Marker 66 may have any suitable length (measured along a direction parallel to longitudinal axis 68 of body 62) that is selected to increase the possibility that marker 66 will be visible to the clinician when therapy delivery member 60 is implanted in patient 14. In the example shown in FIG. 4, marker 66 is positioned only on a part of therapy delivery member 60 that is expected to be visible to the implanting clinician when therapy delivery member 60 is implanted in cranium 18 (FIG. 1) of patient 14 such that therapy delivery member 60 extends through burr hole 16 and fluid delivery port 66 is positioned to deliver a therapeutic agent to a target tissue site. In other examples, marker 66 can extend along the entire length of therapy delivery member 60 or along a greater length of therapy delivery member than that shown in FIG. 4.

Other arrangements of markers are contemplated. In addition, if therapy delivery member 60 defines more than one fluid delivery port, therapy delivery member 60 may include additional markers that indicate the circumferential position (e.g., are circumferentially aligned) with the one or more additional therapy delivery ports. In addition, if therapy delivery member 60 includes a plurality of fluid delivery ports, therapy delivery member 60 may include different markers for the different ports (e.g., a relatively large port being distinguished from a relatively small port with line thicknesses). In addition, in some examples described herein, different types of therapy delivery members (regardless of whether the member includes electrodes, fluid delivery ports, or both) may have different types of markers, such that the markers may be used to indicate the type of therapy delivery member that is implanted in patient 114.

Figure 5:
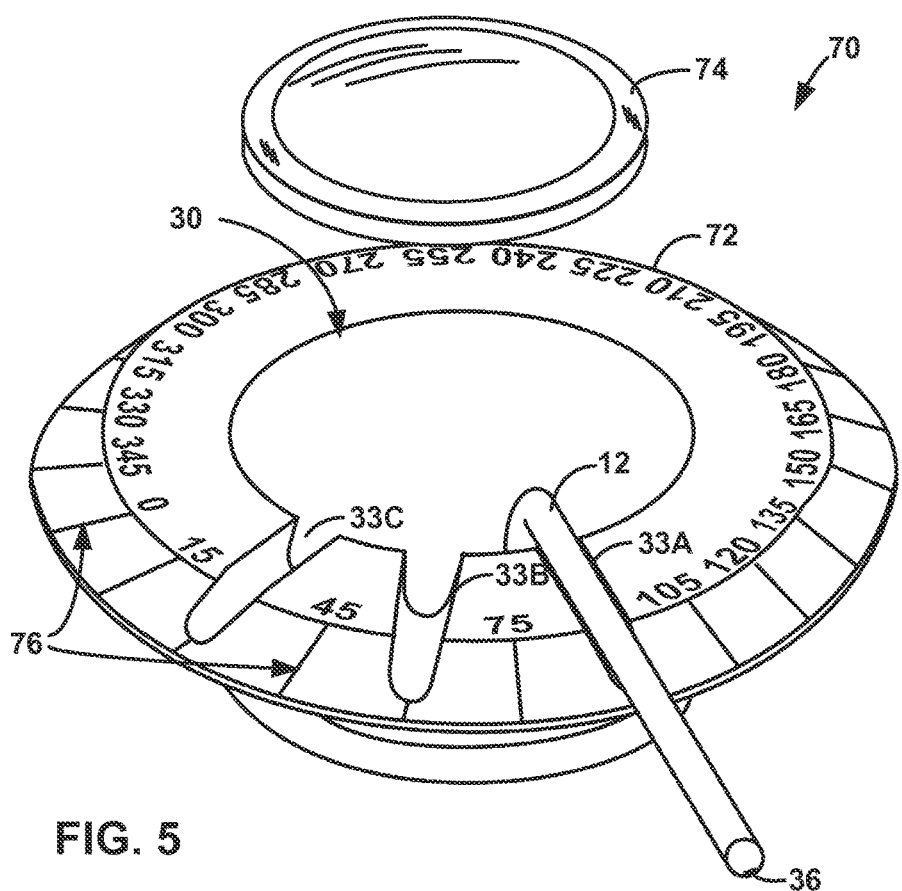
FIG. 5 is a conceptual perspective view of an example burr hole cap assembly that includes a plurality of markings that may indicate a rotational orientation of a therapy delivery member extending through the burr hole cap assembly.

FIG. 5 is a conceptual perspective view of an example burr hole cap assembly 70, which is one example of burr hole cap assembly 20 (FIGS. 1 and 2). Burr hole cap assembly 70 includes base 72 and cover 74, which are similar to base 22 and cover 24 of burr hole cap assembly 20. Base 72 defines opening 30 and a plurality of grooves 33A, 33B, 33C (collectively referred to as "grooves 33"), which are configured to receive therapy delivery member 12 and through which therapy delivery member 12 may exit burr hole cap assembly 70. Base 72 includes a plurality of markers 76 distributed around opening 30. Markers 76 are in fixed positions relative to each other, as well as relative to base 72. For example, markers 76 can include lines or other graphical objects drawn on base 72, etched into base 72, printed onto base 72, or otherwise applied to or formed by base 72. In addition, in some examples, markers 76 can each include a label, such as alphanumeric indicators (as shown in FIG. 5), a unique color, graphical symbols, or the like that helps distinguish one marker from another. In addition, in some examples, markers 76 may be configured to correlate to a marker on therapy delivery element 12. For example, two or more markers 76 may have unique colors that match similar colored markers on therapy delivery element 12.

Markers 76 each indicate a respective location around the perimeter of opening 30, as well as around the perimeter of base 72. In the example shown in FIG. 5, base 72 has a substantially circular cross-sectional shape, and the unit of measurement of markers 76 is degrees (°), such that markers 76 are positioned around the 360° of a circle.

As shown in FIG. 5, in some examples, marker 76 are positioned every 15° around the perimeter of opening 30 of base 72. In other examples, markers 76 can be positioned at any suitable position and with any suitable granularity, such as every 1° to about every 45°, such as about every 35°, in some cases, the granularity provided by markers at every 1° to about every 5° may not be necessary to determine the rotational orientation of therapy delivery after therapy delivery member 12 is implanted in patient 14.

Figure 6:
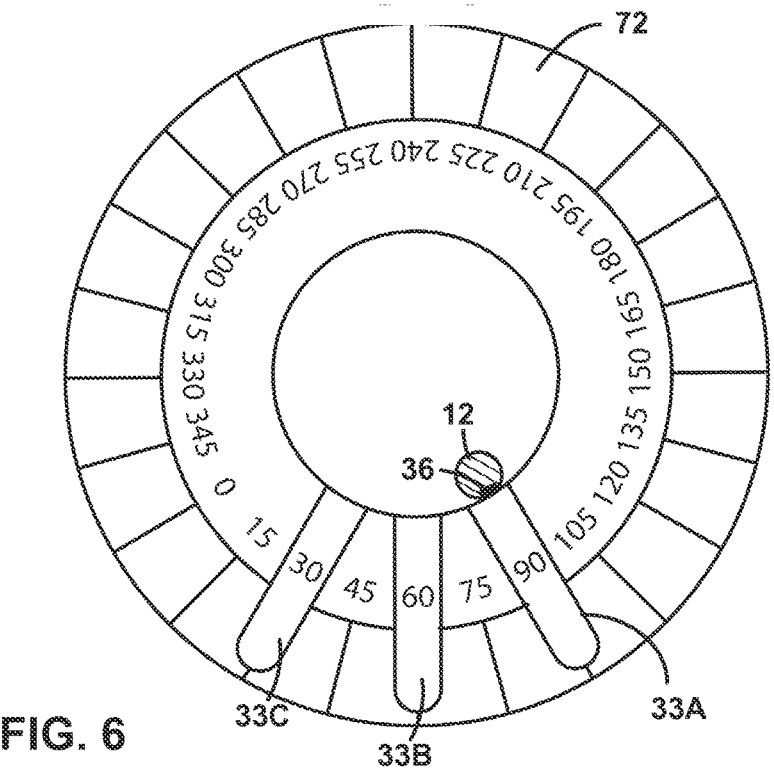
FIG. 6 is a conceptual top view of the example burr hole cap base of FIG. 5 and illustrates a therapy delivery member extending through the burr hole cap assembly base.

FIG. 6 is a conceptual top view of therapy delivery member 12 introduced through opening 30 defined through base 72. A schematic cross-sectional view of therapy delivery member 12 is shown in FIG. 6, as well as in FIGS. 8, 10, and 12, which are discussed below, where the cross-section is taken along a line substantially perpendicular to the longitudinal axis of therapy delivery member 12. The cross-section may be taken at the point along the length of therapy delivery member 12 that extends from opening 30 defined by the base of the respective burr hole cap assembly. Therapy delivery member 12 is illustrated in FIGS. 6, 8, 10, and 12 as extending substantially straight through opening 30 (e.g., substantially parallel to a center axis of opening 30). However, in some cases, therapy delivery member 12 may be implanted at other orientations within opening 30 and may not extend substantially straight through opening 30.

Base 72 may be inserted in burr hole 16 in cranium 18 (FIGS. 1 and 2) of patient 14, and therapy deliver member 12 may be implanted in the brain of patient 14 through base 72, and, therefore, through burr hole 16 through which base 72 extends. Base 72 can be installed in burr hole 16 in a known orientation (e.g., with the 0° marker 76 substantially aligning with a nose of a person), such that markers 76 are in known positions relative to burr hole 16. Because burr hole 16 is in a known position relative to one or more brain structures, markers 76 may indicate the rotational orientation of therapy delivery member 12 relative to burr hole cap assembly 70, from which the rotational orientation of therapy delivery member 12 relative to one or more brain structures of patient 14 may be determined.

Using FIG. 6 as an example, therapy delivery member 12 is implanted such that marker 36 on therapy delivery member 12 is substantially aligned with the 90° marker 76 on base 72 of burr hole cap assembly 70. As discussed above, marker 36 may indicate the circumferential position of a therapy delivery element of therapy delivery member 12. Thus, the marker 76 that is substantially aligned with marker 36 after therapy delivery member 12 is implanted in patient 14 may indicate a meaningful rotational orientation of therapy delivery member 12 in patient 14, e.g., the direction in which a particular electrode or fluid delivery port is facing. In this way, knowledge of the marker 76 of burr hole cap assembly 70 that aligns with marker 36 of therapy delivery member 12 may be used to derive the rotational orientation of the implanted therapy delivery member 12. In this way, markers 76 of burr hole cap assembly 70 can be used after implanting therapy delivery member 12 and burr hole cap assembly 70 in patient 14 and covering burr hole cap assembly 70 with the scalp of patient 14 to determine the rotational orientation of therapy delivery member 12 in patient 14. A clinician may, for example, identify the marker 76 that is known to align with marker 36 of therapy delivery member 12 and determine the orientation of marker 76 relative to one or more target brain structures based on the known implant orientation of burr hole cap base 72.

In some examples, markers 76, and the respective labels, are radiopaque. In these examples, burr hole cap assembly 70 need not be implanted in patient 14 in a known orientation in order to be able to later determine the rotational orientation of therapy delivery member 12 in patient 14, e.g., after burr hole cap assembly 70 is covered by the patient's skin. Markers 76 may also be used to identify whether or not the implanted therapy delivery member 12 has rotated post-implant. Moreover, marker 36 on therapy delivery member 12 need not be radiopaque in order to later determine the rotational orientation of therapy delivery member 12 in patient 14. Rather, at the time therapy delivery member 12 is implanted in patient 14, the clinician may only need to record (e.g., in a handwritten note and/or in an electronic device) intimation that identifies the marker 76 that best aligns with marker 36 of therapy delivery member 12. The rotational orientation of therapy delivery member 12 may be determined at a time following implantation of therapy delivery member 12 in patient 14 by, for example, imaging patient 14 to identify the marker 76 that was recorded as being closest to marker 36 of therapy delivery member 12 and determining the position of the marker 76 relative to one or more brain structures of patient 14 or another anatomical landmark. In this way, in examples in which burr hole cap assembly 70 includes radiopaque markers 76, burr hole cap assembly 70 may be referenced at any time to determine a rotational orientation of therapy delivery member 12 relative to one or more anatomical structures of patient 14.

In other examples of burr hole cap assembly 70, markers 76 may not indicate the position on base 72 in terms of degrees, but, rather, may use other types of labels. For example, markers 76 may each be associated with a respective number or other alphanumeric text. As another example, each marker 76 may be a different color. Markers 76 have a characteristic that distinguishes each marker from an adjacent marker, such that if a clinician indicates therapy delivery member 12 is aligned with a particular marker, the rotational orientation of therapy delivery member relative to base 72 can be determined by locating the particular marker. In any of these examples, if base 72 is installed in burr hole 16 in a known orientation (e.g., with the 0° substantially aligning with a nose of a person), the markers are in known positions relative to burr hole 16, which is in a known position relative to one or more brain structures. In this way, markers 76 may indicate the rotational orientation of therapy delivery member 12 relative to burr hole cap assembly 70, from which the rotational orientation of therapy delivery member 12 relative to one or more brain structures of patient 14 may be determined.

Figure 7:
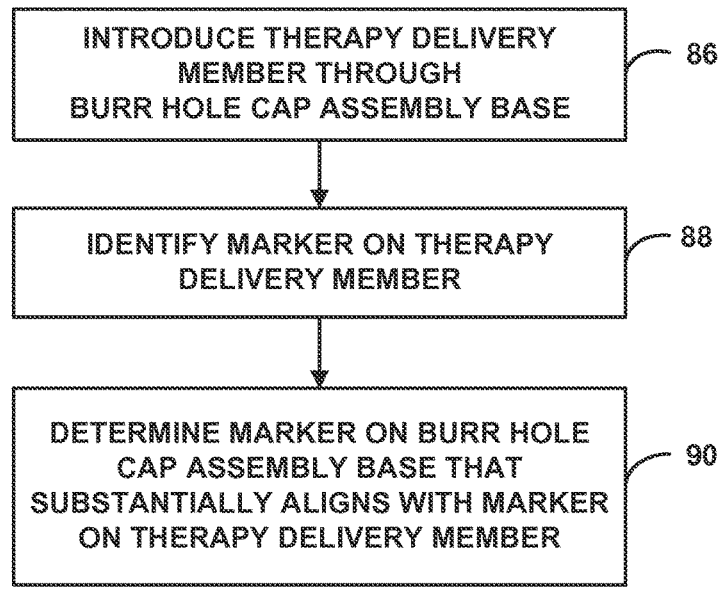
FIG. 7 is a flow diagram illustrating an example technique for determining a rotational position of a therapy delivery member relative to a burr hole cap assembly.

FIG. 7 is a flow diagram illustrating an example technique for determining a rotational position of therapy delivery member 12 relative to a burr hole cap assembly with the aid of a base that includes a plurality of markers. While FIG. 7 is described with respect to burr hole cap assembly 70 (FIGS. 5 and 6), in other examples, the technique shown in FIG. 7 may be used with other burr hole cap assemblies with a plurality of markers.

In accordance with the technique shown in FIG. 7, a clinician may introduce therapy delivery member 12 through opening 30 in burr hole cap base 72 (86). For example, after burr hole cap base 72 is positioned over burr hole 16 (FIGS. 1 and 2) defined through cranium 18 of patient 14, the clinician may introduce therapy delivery member 12 into patient 14 through opening 30 in burr hole cap base 72. In some examples, the clinician utilizes a stereotactic equipment to guide one or more therapy delivery elements of therapy delivery member 12 to the one or more target tissue sites, e.g., in the brain of patient 14.

After therapy delivery member 12 is positioned as desired, the clinician may identify marker 36 on therapy delivery member 12 (88), e.g., by visually ascertaining the location of marker 36. If therapy delivery member 12 has more than one marker, the clinician may also identify those markers, or just identify one marker 36. The clinician may then determine the marker 76 of base 72 that substantially aligns with marker 36 of therapy delivery member 12 (90). The alignment may be, for example, in a radial direction. For example, the clinician may determine which marker 76 of the plurality of markers 76 of base 72 is closest to marker 36 of therapy delivery member 12.

In some examples, the clinician may record information that indicates which marker 76 of the plurality of markers 76 of base 72 substantially aligns with marker 36 of therapy delivery member 12. This information may then be later referenced to determine the rotational orientation of an implanted therapy delivery member 12 in patient 14. In other examples, identification of the marker 76 of the plurality of markers 76 of base 72 that substantially aligns with marker 36 of therapy delivery member 12 may not be recorded for later retrieval, but may instead be determined on an as-needed basis, e.g., by imaging patient 14.

In other examples of burr hole cap assembly 70 and the technique shown in FIG. 7, markers 76 may be positioned on cover 74. In these examples, after positioning cover 74 over base 72, which may not only cover burr hole 16 but substantially fix therapy delivery member 12 in place relative to base 72, the clinician may determine the marker on cover 74 that aligns with marker 36 of therapy delivery member 12. In some examples, marker 36 is identified prior to installation of cover 74 (e.g., in examples in which cover 74 would completely cover marker 36), while in other examples, marker 36 is identified after installation of cover 74 over base 72.

Figure 8:
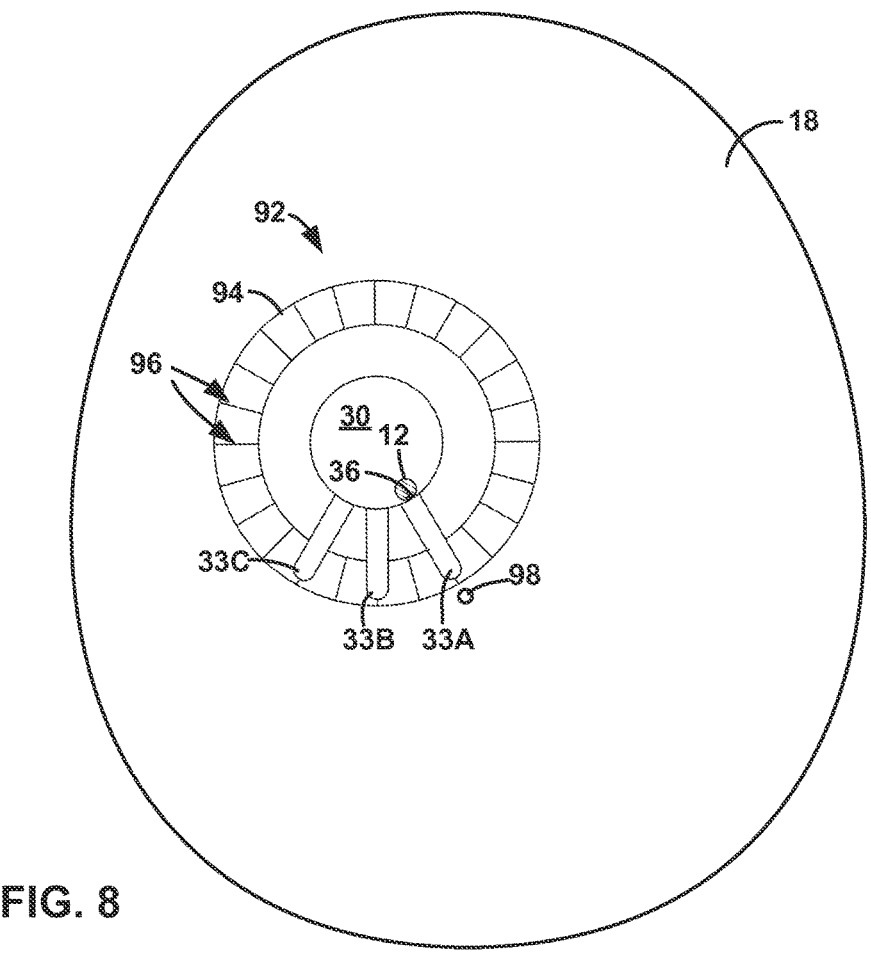
FIG. 8 is a conceptual illustration of another example burr hole cap assembly, which includes a base and a set screw that is movable relative to the base.

FIG. 8 is a conceptual illustration of another example burr hole cap assembly 92, which includes base 94 with a plurality of markers 96 and set screw 98 that is movable relative to base 94. Base 94 may be similar to base 22 of burr hole cap assembly 20 (FIG. 1) in some examples. Although not shown in FIG. 8, in some examples, burr hole cap assembly 92 may include a cover, similar to cover 24 of burr hole cap assembly 20 (FIG. 1) that is configured to fit over base 94 and substantially close opening 30 defined by base 94. Markers 96 may be similar to marker 76 (FIGS. 5-7) in some examples. In the example shown in FIG. 8, however, markers 96 do not include any label or other characteristic (e.g., a color) that distinguishes one marker 96 from another marker 96. Rather, markers 96 are substantially identical marks on base 94. In other examples, markers 96 may be similar to marker 76 (FIGS. 5-7) and may include alphanumeric labels or be color coded.

Set screw 98 is configured to be introduced into cranium 18 of patient 14. Set screw may have any suitable configuration. In some examples, set screw 98 may be partially or fully threaded, and may comprise a head that is wider than the threaded portion of set screw 98. In some examples, set screw 98 is self-tapping, while in other examples, a separate instrument may be used to define an opening in cranium 18 for receiving set screw 98. Set screw 98 may be formed from any suitable material, such as, but not limited to, titanium, biocompatible polymers, or other biocompatible materials. In some examples, set screw 98 comprises a radiopaque material, such that set screw 98 may be detected by medical imaging after set screw 98 is covered by the patient's skin.

After therapy delivery member 12 is implanted in patient 14 through burr hole 16, which is accessed via opening 30 in base 94, a clinician may place set screw 98 in cranium 18 of patient 14 at a location that indicates the rotational orientation of therapy delivery member 12. In the example shown in FIG. 8, for example, set screw 98 is implanted in cranium 18 to indicate the location of marker 36 on therapy delivery member 12. In particular, set screw 98 is substantially radially aligned with marker 36 of therapy delivery member 12. In other examples, set screw 98 may be implanted in cranium 98 to be slightly offset from marker 36, i.e., not substantially radially aligned, but implanted in a manner that indicates the relative location of marker 36 of therapy delivery member 112. Moreover, in some examples, burr hole cap assembly 92 may include more than one set screw 98. For example, two or more set screws may be used to indicate the relative location of marker 36 of therapy delivery member 12, e.g., marker 36 may be positioned midway between the set screws. As another example, if therapy delivery member 12 includes multiple markers, one or more set screws may be used to indicate the relative location of each of the markers of therapy delivery member 12.

Markers 96 of base 94 may be a visual aid to a clinician when the clinician inserts set screw 98 into cranium 18 of patient 14. For example, one or more markers 96 may define a visible line from marker 36 of therapy delivery member 12 to a point on cranium 18 that substantially radially aligns with marker 36, which may be the point at which the clinician may implant set screw 98. In other examples, base 94 of burr hole cap assembly 92 may include any suitable number of markers, such as a fewer or greater number of markers than that shown in FIG. 8. In addition, in other examples, base 94 of burr hole cap assembly 92 does not include markers 96.

In other examples, base 94 or a cap of burr hole cap assembly 92 may be configured to receive set screw 98 and set screw 98 may be configured to be introduced into base 94 or the cap (e.g., instead of cranium 18) to indicate the rotational orientation of therapy delivery member 12. For example, base 94 or the cap may define preconfigured spots for set screw 98 circumferentially located around the edge of base 94 or the cap, and after therapy delivery member 12 is implanted in patient 14 through burr hole 16, a clinician may place set screw 98 in base 94 or the cap at a location that indicates the rotational orientation of therapy delivery member 12. In these examples, base 94 may or may not include markers 96.

Figure 9:
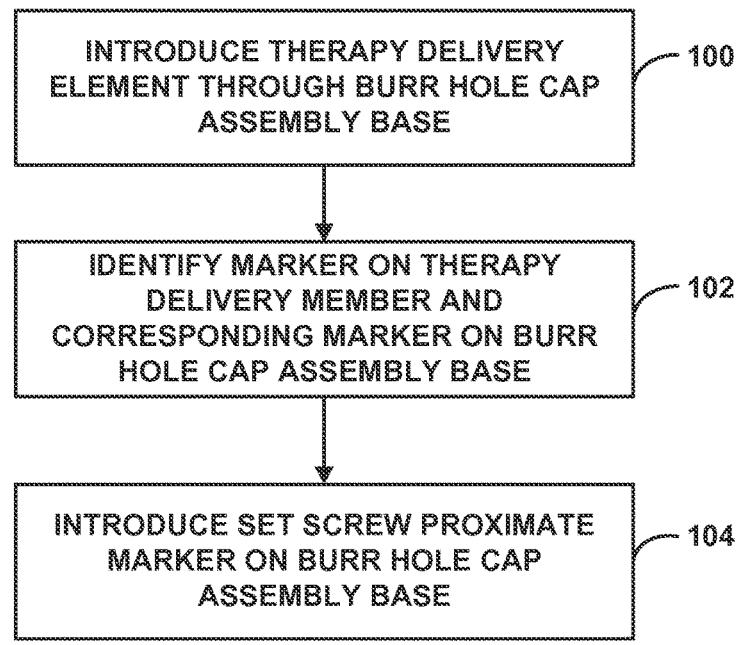
FIG. 9 is a flow diagram illustrating an example technique determining a rotational position of a therapy delivery member relative to a burr hole cap assembly that includes a set screw.

FIG. 9 is a flow diagram illustrating an example technique determining a rotational position of therapy delivery member 12 relative to a burr hole cap assembly that includes a set screw. While FIG. 9 is described with respect to burr hole cap assembly 92 (FIG. 8), in other examples, the technique shown in FIG. 9 may be used with other burr hole cap assemblies that include one or more set screws.

In accordance with the technique shown in FIG. 9, a clinician may introduce therapy delivery member 12 through opening 30 in burr hole cap base 94 (100). For example, after burr hole cap base 94 is positioned over burr hole 16 (FIGS. 1 and 2) defined through cranium 18 of patient 14, the clinician may introduce therapy delivery member 12 into patient 14 through opening 30 in burr hole cap base 94. After therapy delivery member 12 is positioned as desired, the clinician may identify marker 36 on therapy delivery member 12 and a corresponding marker on base 94 (102), e.g., by visually ascertaining the location of marker 36 and a marker 96 that best radially aligns with marker 36. The clinician may then introduce set screw 98 in cranium 18, base 92, or another part of assembly 92 proximate to the identified marker 96 on base 94 (104).

After therapy delivery member 12 is implanted in patient 14 and after burr hole cap assembly 92 is covered up by the patient's skin, the rotational orientation of therapy delivery member 12 may be determined based on information provided by set screw 98. In examples in which set screw 98 comprises a radiopaque material, set screw 98 may be visible in a medical image. By identifying set screw 98 in the image, the clinician may also determine the orientation of therapy delivery member 12, i.e., by determining that marker 36 is substantially aligned (e.g., radially aligned) with set screw 98. In other examples, markers 96 may be positioned on a cover of burr hole cap assembly 92. In these examples, the clinician may insert set screw 98 in cranium 18 or the cap after the cover is placed over base 94.

If therapy delivery member 12 has more than one marker, and burr hole cap assembly 92 includes more than one set screw, the technique shown in FIG. 9 may be repeated for the additional markers of therapy delivery member 12.

Burr hole cap assembly 92 provides information that indicates the rotational orientation of therapy delivery member 12 relative to burr hole cap assembly 92, which, as discussed above, may be used to determine the orientation of one or more therapy delivery elements (e.g., electrodes or fluid delivery ports) in patient 14. This information may be obtainable from burr hole cap assembly 92 without imaging patient 14 after burr hole cap assembly 92 is covered by skin of patient 114. For example, in some examples, set screw 98 is implanted so that it protrudes from cranium 18 and is detectable via palpation. A clinician may palpate the patient's scalp to find set screw 98 and burr hole cap assembly 92. After finding set screw 98 and burr hole cap assembly 92, the clinician may determine that therapy delivery member 12 is implanted in patient 14 such that marker 36 faces set screw 98. In this way, the clinician may determine the direction in which the one or more therapy delivery elements of therapy delivery member 12 face within patient 114, and relative to one or more brain structures of patient 14.

In some examples, set screw 98 comprises a radiopaque material, such that set screw 98 may be detected by medical imaging after set screw 98 is covered by the patient's skin. In these examples, the clinician may determine the rotational orientation of therapy delivery member 12 relative to burr hole cap assembly 92 by imaging patient 14 to determine the location of set screw 98.

In addition, in some examples in which markers 96 are associated with unique identifiers (e.g., alphanumeric identifiers or a unique color), the clinician may record information that indicates which marker 96 of the plurality of markers 96 of base 94 substantially aligns with marker 36 of therapy delivery member 12. If base 94 is implanted in burr hole 16 in a known orientation or if markers 96 are radiopaque, this information may then be later referenced to determine the rotational orientation of one or more therapy delivery elements of an implanted therapy delivery member 12 in patient 14.

Figure 10A:
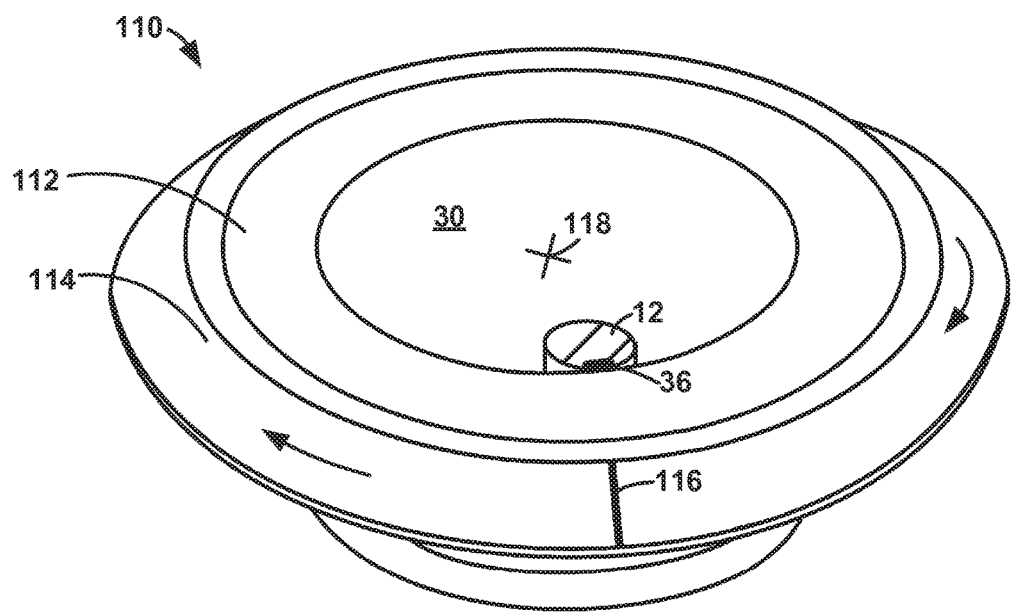
FIG. 10A is a conceptual perspective view of a part of another example burr hole cap assembly, which includes a base and a rotating member comprising a marker.
Figure 10B:
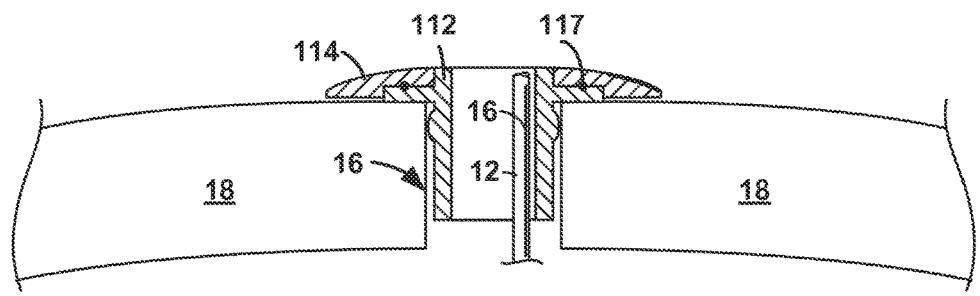
FIG. 10B is a conceptual cross-sectional illustration of the burr hole cap assembly shown in FIG. 10A.

FIG. 10A is a conceptual perspective view of another example burr hole cap assembly 110, which includes base 112 and rotating member 114 including a marker 116. FIG. 10B is a schematic and conceptual cross-sectional illustration of base 112, rotating member 114, and therapy delivery member 12, where base 112 is implanted in burr hole 16 in cranium 18 of patient 14. Base 112 defines opening 30 configured to receive therapy delivery member 12. Although not shown in FIGS. 10A and 10B, burr hole cap assembly 110 may include a cover, such as cover 24 of burr hole cap assembly 20 (FIGS. 1 and 2), that is configured to fit over base 112 and rotating member 114 and substantially close opening 30 defined by base 112. In some examples, the cover may also substantially fix a position of therapy delivery member 12 relative to base 112 and rotating member 114.

Rotatable member 114 and base 112 may have similar cross-sectional geometries (e.g., circular in the example shown in FIGS. 10A and 10B) or different cross-sectional geometries. Rotatable member 114 is mechanically coupled to base 112 and is configured to rotate relative to base 112, e.g., around center axis 118 that is common to both base 112 and rotatable member 114. For example, rotatable member 114 may be mounted to base 112 on bearings 1117, as shown in FIG. 10B. In addition or instead, rotatable member 1114 may be mounted to base 112 via a set of gears or friction fit bushings. As another example, rotatable member 114 and base 112 may have similarly shaped surfaces that slidably engage such that rotatable member 114 may slide relative to base 112, which mains relatively stationary relative to burr hole 16 (FIGS. 1 and 2). In some examples, rotatable member 114 is configured to rotate in only one direction relative to base 112. For example, rotatable member 114 may be mounted to base via a ratcheting mechanism. Rotatable member 114 may be rotated continuously about axis 118 in some examples, while in other examples, rotatable member 114 has predetermined, discrete positions relative to base 112 (e.g., the positions associated with each tooth boundary in the case of a ratcheting mechanism).

Burr hole cap assembly 110 includes a mechanism that substantially fixes the rotational position of rotatable member 114 relative to base 1112. In examples in which rotatable member 114 is mounted to base 112 via a ratcheting mechanism, for example, the ratcheting mechanism may include a spring loaded finger that engages with teeth of a gear; the rotational position of rotatable member 114 relative to base 112 may be substantially fixed by the spring until a force sufficient to overcome the spring force disengages the spring from the teeth. One or more other mechanisms may be used to substantially fix the rotational position of rotatable member 114 relative to base 112, such as one or more set screws, slide locks (e.g., comprised of a tooth on either member 114 or base 1112 that slide engages notches on the other one of member 114 or base 112), friction between rotatable member 114 and base 112, an adhesive, or crimping of rotatable member 114 to base 112 (e.g., via a tool or by application of force by the clinician's fingers). In addition, in some examples, application of cover 24 of burr hole cap assembly 110 may substantially lock rotating member 114 in place relative to base 112.

Marker 116 may be similar to other markers 76 (FIGS. 5 and 6) and markers 96 (FIG. 8) described herein. In some examples, marker 116 comprises a radiopaque material that is visible in a medical image. In addition, marker 116 can be visible to the human eye without the aid a visualization instrument. In some examples, marker 116 protrudes from a major surface of rotating member 114, while in other examples, marker 116 is substantially flush with rotating member 114.

Marker 116 has a fixed position relative to rotatable member 114, such that as rotatable member 114 rotates relative to base 112, marker 116 moves relative to base 112. This configuration enables a clinician to manipulate rotatable member 114 until marker 116 is positioned to indicate the rotational orientation of therapy delivery member 12 relative to base 112.

Figure 11:
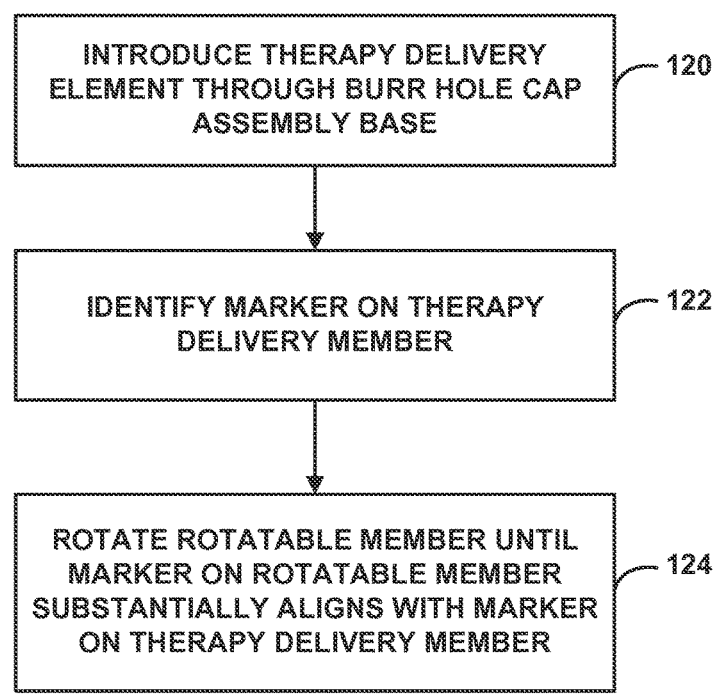
FIG. 11 is a flow diagram of an example technique for indicating a rotational position of a therapy delivery member relative to a burr hole cap assembly that includes a rotatable member with a marker, where the rotatable member rotates relative to a base of the burr hole cap assembly that is configured to fit in a burr hole.

FIG. 11 is a flow diagram of an example technique for indicating a rotational position of therapy delivery member 12 relative to a burr hole cap assembly that includes a rotatable member with a marker, where the member rotates relative to a base of the burr hole cap assembly that is configured to fit in a burr hole. While FIG. 11 is described with respect to burr hole cap assembly 110, in other examples, the technique shown in FIG. 11 may be used with other burr hole cap assemblies.

In accordance with the technique shown in FIG. 11, a clinician may introduce therapy delivery member 12 through opening 30 in burr hole cap base 112 (120). For example, after base 112 is positioned over burr hole 16 (FIGS. 1 and 2) defined through cranium 18 of patient 14 and base 112 is substantially fixed relative to burr hole 16, the clinician may introduce therapy delivery member 12 into patient 14 through opening 30 in base 112. After therapy delivery member 12 is positioned as desired, the clinician may identify marker 36 on therapy delivery member 12 (122). Thereafter, the clinician may rotate rotatable member 114 until marker 116 substantially aligns (e.g., radially aligns) with marker 36 (124). For example, the clinician may rotate rotatable member 114 until marker 116 is adjacent marker 36, as shown in FIG. 10A.

In some cases, therapy delivery member 12 may be implanted in patient 14 such that marker 36 is not directly adjacent base 112 (as shown in FIG. 10A), but, rather, is positioned to be aligned with a part of base 112 not in contact with therapy delivery member 12. For example, therapy delivery member 12 may be implanted in patient 14 such that marker 36 is rotated about 180° about a longitudinal axis of therapy delivery member 12 relative to the orientation shown in FIG. 10A. In these cases, marker 116 of rotatable member 114 may be relatively far from therapy delivery member 12 (e.g., may be rotated about 180° about axis 118 relative to the orientation shown in FIG. 10A), but may still indicate the rotational orientation of therapy delivery elements of member 12 in patient 14. Therapy delivery member 12 need not be directly adjacent marker 114 of rotatable member 114 in order for the rotational orientation of markers 36, 116 to be aligned.

After therapy delivery member 12 is implanted in patient 14 and after burr hole cap assembly 110 is covered up by the patient's skin, the rotational orientation of therapy delivery member 12 may be determined based on information provided by marker 116. In examples in which marker 116 comprises a radiopaque material, marker 116 may be visible in a medical image. Thus, a clinician can generate a medical image of patient 14 and burr hole cap assembly 110 and identify marker 116 in the medical image to determine the orientation of therapy delivery member 12 relative to burr hole cap assembly base 112. In examples in which marker 116 protrudes from assembly 110 or is otherwise detectable by palpation, the clinician may palpate patient 14 to determine the position of marker 116.

The clinician may determine the rotational orientation of therapy delivery member 12 in patient 14 based on the information indicating the position of marker 116 relative to, e.g., cranium 18 (FIG. 1) of patient 14. For example, the clinician may determine that marker 36 is substantially aligned (e.g., radially aligned) with marker 116, and may determine that burr hole cap assembly 110, including marker 116, has a known orientation (in three dimensional space) relative to one or more anatomical structures of patient 114. Thus, by relating the rotational orientation of therapy delivery member 12 to burr hole cap assembly 110 and relating the orientation of burr hole cap assembly 110 to one or more anatomical structures of patient 14, the clinician may determine the orientation of therapy delivery member 12 relative to one or more anatomical structures of patient 14.

If therapy delivery member 12 includes a plurality of markers, the clinician may choose which marker of therapy delivery member 12 with which the marker 116 of burr hole cap assembly 110 should be aligned. The clinician may then record information that indicates the marker of therapy delivery member 12 with which marker 116 is aligned.

Figure 12:
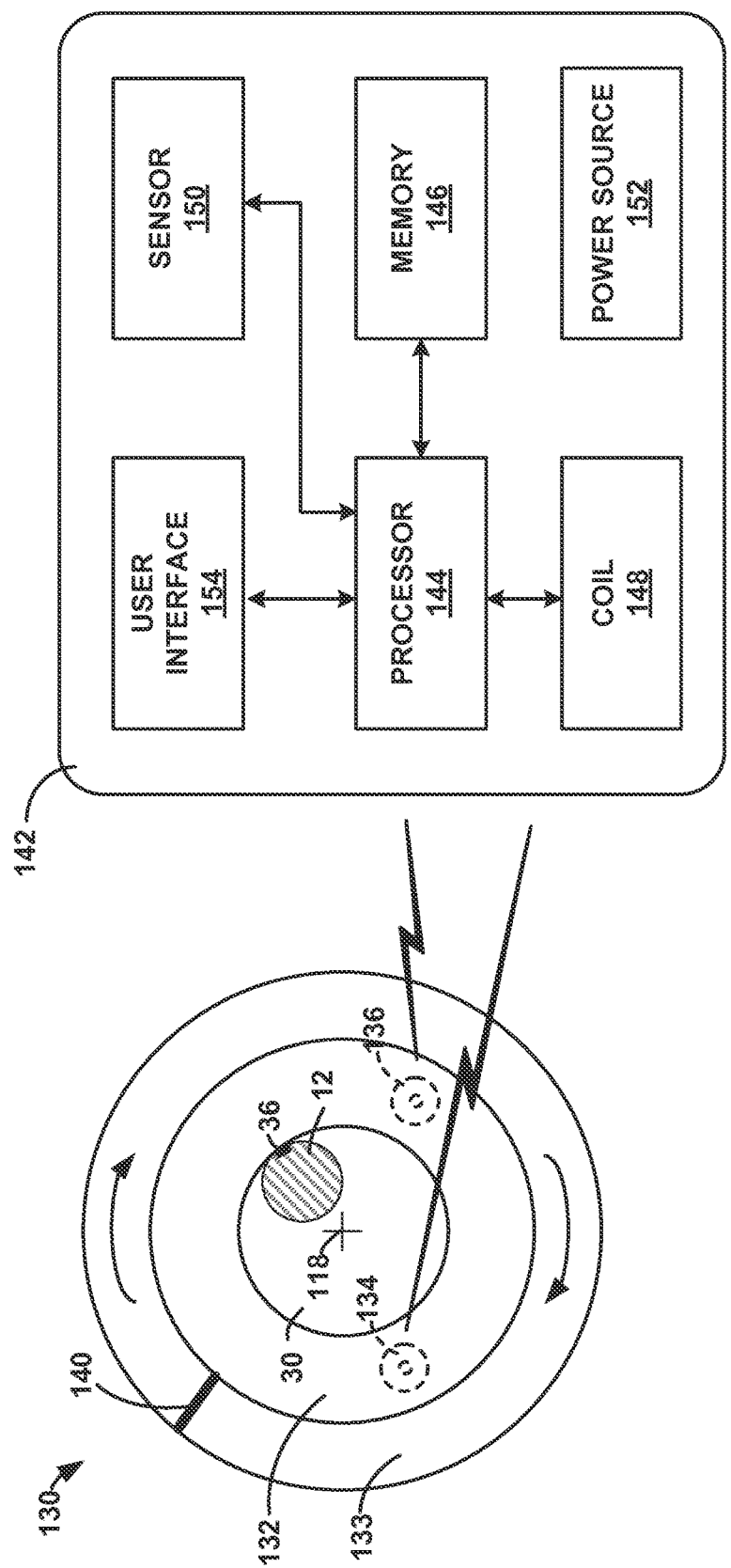
FIG. 12 is a conceptual top view of another example burr hole cap assembly, which includes inductors, the inductive reactances of which indicate a rotational orientation, of a therapy delivery member extending through an opening defined by a base of the assembly, and a functional block diagram of a reader device.

FIG. 12 is a conceptual top view of burr hole cap assembly 130, which includes burr hole cap assembly base 132 and rotatable member 133. Also shown in FIG. 12 is a functional block diagram of reader device 142, which is described in further detail below. Burr hole cap assembly base 132 may be similar to burr hole cap assembly base 112 (FIG. 10) and defines opening 30 that is configured to receive a therapy delivery member. Although not shown in FIG. 12, burr hole cap assembly 130 may include a cover, which can be similar to cover 24 of burr hole cap assembly 20 (FIG. 2). The cover may be configured to be mechanically connected to base 132, and may also be configured to substantially fix therapy delivery member 12 in place relative to burr hole 16 in cranium 18 (FIG. 1), as well as substantially cover burr hole 16.

Figure 13A:
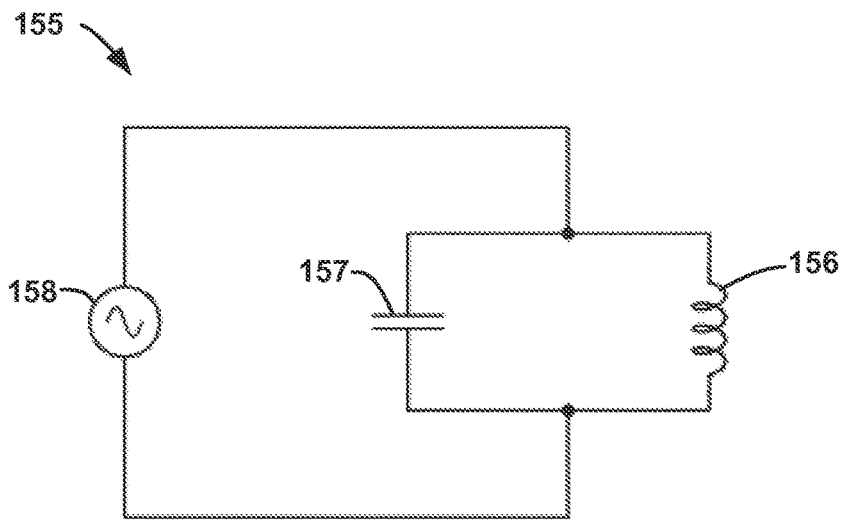
FIGS. 13A-13C are schematic circuit diagrams of example reactive elements that can be included in a burr hole cap assembly, where the reactive elements are each configured to indicate a rotational orientation, of a therapy delivery member relative to the burr hole cap assembly.
Figure 13B:
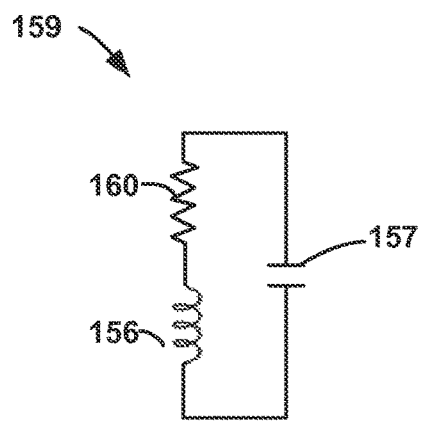
Figure 13C:
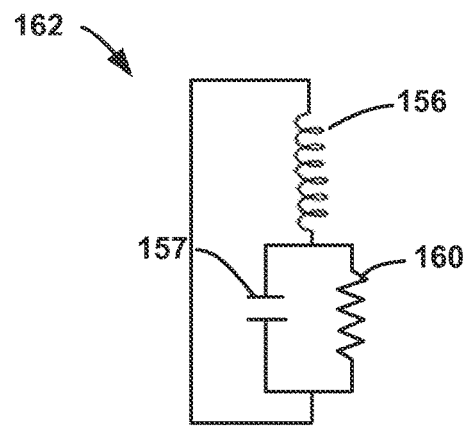

Burr hole cap assembly base 132 includes two reactive elements, which in the example shown in FIG. 12, includes inductors 134, 136 electrically connected to at least one other electrical component (e.g., one or more capacitors and/or resistors), such that each of the inductors 134, 136 is a part of a respective circuit (separate circuits). Example reactive elements including an inductor (e.g., inductor 134 or inductor 136) are shown in FIGS. 13A-13C and described in further detail below. The circuits in which inductors 134, 136 are included may be, for example, passive circuits that do not have their own power source. Rather, as discussed below, the circuits can be powered by an external device, e.g., via inductive coupling.

The circuits in which inductors 134, 136 are included may be, for example, resonant circuits. For example, in some examples, each inductor 134 is electrically connected to a capacitor, and, in some cases, a resistor, in parallel or in series to form an electrical harmonic oscillator, which is configured to store electrical energy oscillating at a resonant frequency of the circuit. The inductive reactance of the circuit may change as a function of the resonant frequency of the inductor 134 or 136 in the circuit, such that the resonant frequency of the circuit may be indicative of the inductive reactance of the inductor. One or both inductors 134, 136 may be configured to radiate energy effectively when resonant, or the respective circuit may include (in addition to the inductive or capacitive elements), an antenna element.

The resonant frequency of an inductor can be determined based on the following equation:

$$XL = 2*pi*f*L \quad \text{(Equation 1)}$$

In the above equation, XL is the inductive reactance, f is the resonant frequency, and L is the inductance value of the inductor. The inductance L of inductors 134, 136 are known values, e.g., are a property of the inductors 134, 136 that is known at the time the inductors 134, 136 are positioned in base 132. Thus, if the resonant frequency of the inductor is determined, the value of the inductive reactance of the inductor may be determined using Equation 1. In order to determine the rotational orientation of marker 140 relative to base 132, a parameter indicative of the inductive resonance can be determined, such as the resonant frequency.

FIG. 13A is a schematic circuit diagram of an example reactive element 155 that can be included in burr hole cap base 132. Reactive element 155 includes inductor 156 and capacitor 157 connected in parallel, and voltage source 158, which can be, for example, provided by an external device (e.g., reader device 142 discussed in further detail below or a medical device programmer). Inductor 156 may be, for example, inductor 134, 136 discussed above with respect to FIG. 12. Reactive element 155 is configured to resonate when the reactances of inductor 156 and capacitor 157 are substantially equal to each other.

The reactance of capacitor 157 can be determined based on the following equation:

$$XC = 1/(2*pi*f*C) \quad \text{(Equation 2)}$$

In the above equation, XC is the capacitive reactance, f is the resonant frequency, and C is the capacitance value of the inductor. The inductance C of capacitor 157 is a known values because it is a property of capacitor 157.

In some examples, reactive element 156 may include a coil and a rectifier and the external power source may energize the coil and rectifier, rather than directly energizing the inductor. Thus, a current can be induced by an external magnetic field in the circuit including inductor 156 through the coil and rectifier, which then apply the current across inductor 156 and capacitor 157.

FIG. 13B is a schematic circuit diagram of another example reactive element 159 that can be included in burr hole cap base 132. Reactive element 159 includes inductor 156 and capacitor 157 connected in parallel, and resistor 160 connected in series with inductor 156. FIG. 13C is a schematic circuit diagram of another example reactive element 162 that can be included in burr hole cap base 132. Reactive element 162 includes inductor 156 and capacitor 157 connected in series, and resistor 160 connected in parallel with capacitor 157.

In some examples, the circuits shown in FIGS. 13A-13C, as well as other example reactive elements, may be connected to an antenna coil that collects the energy from the circuit and allows resonance to occur. In other examples, inductor 156 in the circuit may act as an antenna coil, and capacitor 157 and, in some examples, resistor 160, are selected to resonate at a desired frequency. For example, an external device (e.g., reader device 142 or a programmer) may generate power that induces a current in inductor 156, which may then emit a resonant signal that is sensed by the external device. A processor of the external device may then determine a parameter indicative of the inductive reactance of inductor 156 based on the resonant signal, e.g., based on the resonant frequency or by using Equation 1 to determine the resonant frequency.

Returning now to FIG. 12, inductors 134, 136 and their respective circuits are in fixed positions relative to each other, as well as relative to the body that defines base 132. Inductors 134, 136 of base 132 are passive electrical components that, together with their circuits, are configured to store energy in a magnetic field as electrical current passes through respective conductors. Inductors 134, 136 may each have any suitable configuration, and may be, but need not be, identical in construction. In some examples, inductors 134, 136 each comprise an electrical conductor (e.g., copper wire or another type of wire) shaped as a coil, thereby defining a conductive coil. The conductor may be wrapped around air or a ferrous material in some examples, although other types of inductors can also be used. The coil can be circular in cross-section, quadrilateral (e.g., square or rectangular) in cross-section, or have any suitable cross-sectional shape. Inductors 134, 136 may each be configured to be energized in the presence of a magnetic field.

In the example shown in FIG. 12, rotatable member 133 may be similar to rotatable member 114 (FIG. 10), but includes ferromagnetic marker 140, which is comprised of a ferromagnetic material. Rotatable member 133 may be configured to rotate relative to base 132, e.g., using the mechanisms described above with respect to member 114. Examples of suitable ferromagnetic materials include, but are not limited to, iron (Fe), cobalt (Co), nickel (Ni), or any combinations thereof. In other examples, marker 140 can be comprised of other materials that affect the flow of magnetic fields. Marker 140 is visible to the human eye without the aid of medical imaging, and, in some examples, may also be radiopaque.

Ferromagnetic marker 140 is at a fixed position on rotatable member 133, such that as rotatable member 133 rotates relative to base 132, marker 140 rotates relative to base 132, and, therefore, relative to inductors 134, 136. Ferromagnetic marker 140 is positioned at a predetermined circumferential position on rotatable member 133. Ferromagnetic marker 140 may have any suitable dimension. The size and geometry of ferromagnetic marker 140, as well as the placement on rotatable member 133 (e.g., the distance relative to center axis 118 of cap 132) are selected such that marker 140 is configured to cause desired, appreciable changes in the inductive reactances of inductors 134, 136 that can be sensed by a reader device, such as reader device 142, which is discussed in further detail below. In some examples, the proximity of marker 140 to inductors 134, 136, the size of inductors 134, 136, and material properties of ferromagnetic marker 140 may also affect the affect of ferromagnetic marker 140 on the inductive reactances of inductors 134, 136. Thus, in some cases, the configuration of ferromagnetic marker 140 may be selected such that even when rotatable member 133 is rotated to a position in which ferromagnetic marker 140 is as far from inductors 134, 136 as possible, marker 140 may still cause appreciable changes in the inductive reactances of inductors 134, 136.

As with marker 116 of rotatable member 114 (FIG. 10), ferromagnetic marker 140 can be substantially aligned with marker 36 of therapy delivery member 12 by rotating rotatable member 133, such that marker 140 indicates the rotational orientation of therapy delivery member 12 relative to base 132. After therapy delivery member 12 is introduced through opening 30 in base 132 and positioned in patient 14 as desired, the clinician may identify marker 36 on therapy delivery member 12 and rotate rotatable member 133 until marker 140 substantially aligns (e.g., radially aligns) with marker 36 (124). For example, the clinician may rotate rotatable member 114 until marker 116 is adjacent marker 36, as shown in FIG. 12.

The proximity of ferromagnetic marker 140 to inductors 134, 136 may change the inductive reactances of the inductors 134, 136. Depending on the rotational orientation of rotatable member 133 relative to base 132, the proximity of ferromagnetic marker 140 to inductors 134, 136 may change, and the proximity of ferromagnetic marker 140 to inductors 134, 136 may change the inductive reactances of inductors 134, 136. On at least this principle, the rotational orientation of therapy delivery member 12 relative to base 132 may be determined with the aid of marker 140.

In other examples, ferromagnetic marker 140 may not be visible and may be positioned in (or on) rotatable member 133 at a fixed position relative to a visible marker (e.g., visible marker 116 shown in FIG. 10A). In some examples, ferromagnetic marker 140 is not aligned with the visible marker, while in other examples, ferromagnetic marker 140 is aligned (e.g., overlaps) with the visible marker. In either case, the rotation of the visible marker relative to base 132 and inductors 134, 136 may also result in rotation of ferromagnetic marker 140 relative to inductors 134, 136, which may cause detectable changes in the inductive reactances of inductors 134, 136 that can be sensed by a reader device, such as reader device 142. The changes in the inductive reactances of inductors 134, 136 may be associated with a particular position of the visible marker.

In addition, although one ferromagnetic marker 140 is shown in FIG. 12, in other examples, rotatable member 133 may include more than one ferromagnetic marker that is in fixed position relative to a visible marker, such that changes in the inductive reactances of inductors 134, 136 caused by the position of the ferromagnetic markers may be associated with a particular position of the visible marker.

To determine the inductive reactance of inductor 134, inductor 134 may be energized and one or more properties (e.g., the magnetic flux) of the magnetic field generated by inductor 134 may be sensed. The energization of inductor 134 causes current to flow in the conductive coil of inductor 134 and the circuit of which inductor 134 is a part. The circuit including inductor 134 has a resonant frequency that is related to the inductive reactance of inductor 134 (see Equation 1 above), such that determining a frequency at which the circuit oscillates once energized allows the inductive reactance of the inductor 134 to be determined. In some examples, the frequency at which the circuit oscillates may be determined by monitoring the magnetic or electric fields the circuit radiates back to the energizing system, which may be reader device 142 in some examples, and determining a frequency of the oscillation of electrical and/or magnetic components of the electromagnetic field. The inductive reactance of inductor 136 can similarly be determined.

In some examples, marker 140 may be designed in a way so as to minimally interfere with MRI scans, e.g., by appropriately adjusting the configuration (e.g., size, shape, material, or any combination thereof) of marker 140 or a mechanism of action by which marker 140 indicates the rotational orientation of therapy delivery element 12. For example, a second coil may be used to load a primary coil, but tuned such that MRI interaction is minimized, e.g., to cause less distortion in a magnetic resonance environment.

In some examples, a reader device 142 can be used to determine the inductive reactance of each of the inductors 134, 136. Reader device 142 shown in FIG. 12 includes processor 144, memory 146, coil 148, sensor 150, power source 152, and user interface 154. Reader device 142 comprises any suitable arrangement of hardware, alone or in combination with software and/or firmware, to perform the techniques attributed to reader device 142. In various examples, processor 144 may include one or more processors, such as one or more microprocessors, controllers, digital signal processors (DSPs), application specific integrated circuits (ASICs), field-programmable gate arrays (FPGAs), or equivalent discrete or integrated logic circuitry. Memory 146 may include, for example, any volatile or non-volatile media, such as a random access memory (RAM), read only memory (ROM), non-volatile RAM (NVRAM), electrically erasable programmable ROM (EEPROM), flash memory, and the like. Although processor 144, coil 148, and sensor 150, are described as separate modules, in some examples, processor 144, coil 148, and sensor 150 can be functionally integrated. In some examples, processor 144, coil 148, and sensor 150 correspond to individual hardware units, such as ASICs, DSPs, FPGAs, or other hardware units. Power source 152 delivers operating power to the components of reader device 142. Power source 152 may include a rechargeable or non-rechargeable battery and a power generation circuit to produce the operating power.

Under the control of processor 144, coil 148 (e.g., an inductor similar to one or both inductors 134, 136) is energized with power from power source 152 to generate a magnetic field (or electric field in some examples) that is configured to energize a proximate inductor 134, 136. In addition, under the control of processor 14, sensor 150 senses the magnetic flux or other property of the magnetic field generated by the energized inductor 134 or 136, which can indicate the inductive reactance of the inductor 134, 136. For example, processor 144, with the aid of sensor 150, may determine the frequency at which the circuit including the inductor 134, 136 being monitored oscillates once energized by monitoring the magnetic or electric fields the circuit radiates back to sensor 150. As discussed above, the frequency of oscillation (also referred to as a resonant frequency) is indicative of the inductive reactance of the respective inductor 134 or 136 (see Equation 1). As a result, once processor 144 determines the resonant frequency of the circuit, the inductive reactance may be determined using Equation 1 and the known inductance value of the respective inductor 134, 136.

As discussed in detail below, a parameter indicative of the inductive reactance of the inductor can be associated with a particular rotational position of marker 140 relative to base 132, where the parameter can be, for example, the resonant frequency, the inductive reactance, a ratio of resonant frequencies of inductors 134, 136, a ratio of inductive reactances of inductors 134, 136, and the like. That is, each of a plurality of rotational positions of marker 140 may be associated with a unique parameter indicative of the inductive reactance. Accordingly, processor 144 may access a data structure or the like to determine the rotational position of marker 140 relative to base 132 associated with the determined parameter indicative of the inductive reactance of the inductor. Based on Equation 1, the resonant frequency may be directly indicative of the inductive reactance, such that the frequency may be a surrogate for the inductive reactance.

In some examples, coil 148 can be used to both energize inductors 134, 136 and sense the properties of each of the magnetic fields generated by the energized inductors 134, 136, i.e., in some examples, sensor 150 may comprise coil 148. In some examples, memory 146 stores the values of sensed resonant frequencies, determined inductive reactance values, other values related to determining the rotational orientation of marker 140 relative to base 132, as well as any software necessary for the operation of reader device 142.

In some examples, user interface 154 may include a display screen and one or more input buttons that allow reader device 142 to receive input from a user. In some examples, the display may be, for example, a liquid crystal display (LCD), light emitting diode (LED) display, or a touch screen. The input buttons may include a touch pad, increase and decrease buttons, emergency shut off button, alphanumeric keypad or a reduced set of keys associated with particular functions, and/or other buttons needed to control interrogation of inductors 134, 136 and other functions provided by reader device 142. In some cases, the user may interact with user interface 154 via a stylus, soft keys, hard keys, directional devices, and any of a variety of other input media.

A user may interact with user interface 154 to control reader device 142. For example, in some examples, user interface 154 may comprise input buttons or the like that enable a user to initiate the interrogation of inductors 134, 136, store the determined inductive reactances of inductors 134, 136, determine the relative orientation of therapy delivery member 12 relative to base 132 based on the determined inductive reactances, and the like. In addition, in some examples, processor 144 controls user interface 154 to provide information to the user. For example, processor 144 may display determined inductive reactances values (or ratio of values) via the display screen of user interface 154. As another example, processor 144 may display, via the display screen of user interface 154, the distances between markers 140 and inductors 134, 136, the ratio of such distances, or rotational orientation of marker 140 determined by processor 144 based on determined inductive reactance values or sensed resonant frequencies.

In some examples, the inductive reactance of inductor 134 can be associated with a distance between ferromagnetic marker 140 and inductor 134 and the inductive reactance of inductor 136 can be associated with a distance between ferromagnetic marker 140 and inductor 136. Thus, in some examples, a plurality of inductive reactance values and associated distances can be predetermined and stored (e.g., by memory 146 of reader device 142 or another external device, or by an implanted device, such as a medical device) for each inductors 134, 136. The stored distances can be radial in some examples in which base 132 and rotatable member 133 are substantially circular in cross-section. In other examples, the stored distances can be linear.

The distances between marker 140 and inductors 134, 136 are based on the rotational orientation of rotatable member 133 relative to inductors 134, 136. For example, as rotatable member 133 is rotated in a clockwise direction relative to the rotational orientation shown in FIG. 12, the distance between marker 140 and inductor 134 may increase, while the distance between marker 140 and inductor 136 may decrease. Thus, when marker 140 is substantially aligned with marker 36 of therapy delivery member 12, various values determined based on the inductive reactances of inductors 134, 136 may be used to approximate the rotational orientation of therapy delivery member 12 relative to base 132. For example, in one example, the ratio of the distance between marker 140 and inductor 134 to the distance between marker 140 and inductor 136 may be used to approximate the rotational orientation of marker 140 (and, therefore, therapy delivery member 12) relative to base 132.

As another example, a ratio of the inductive reactances of inductors 134, 136 may be used to approximate the rotational orientation of marker 140 relative to base 132. In yet another example, the absolute inductive reactance values of inductors 134, 136 or the individual distance values between marker 140 and inductors 134, 136 may be associated with a specific rotational orientation of marker 140 relative to base 132. In other examples, the sum of distances of marker 140 from each of the inductors 134, 136 can be associated with the approximate rotational orientation of therapy delivery member 12 relative to base 132. Thus, a plurality of rotational orientations of marker 140 (e.g., expressed in terms of degrees around the circular perimeter of base 132, where the 0° degree mark is at a known position of base 132, expressed in terms of radians, or sectors or quadrants of base 132) can be associated with any one or more of respective inductive reactance values of each of inductors 134, 136, a respective ratio of inductive reactance values of inductors 134, 136, a ratio of distances between marker 140 and each inductor 134, 136, the sum of distances between marker 140 and each inductor 134, 136 and the like. These values may be stored by memory 146 of reader device 142 or by another device.

Determining the distances between ferromagnetic marker 140 of rotatable member 133 and two inductors 134, 136 of burr hole cap assembly 130 may help better approximate the rotational orientation of ferromagnetic marker 140 relative to base 132 compared to burr hole cap assemblies that include only one inductor. The inductive reactances of inductors 134, 136 may indicate not only the distance between one or both inductors 134, 136 and marker 140, but also the direction of marker 140 relative to inductors 134, 136. On the other hand, an inductive reactance of a single inductor 134 may indicate that marker 140 is a certain distance way, but may not indicate which direction (e.g., clockwise or counterclockwise) the distance is measured. In addition, with one inductor, ferromagnetic marker 140 may have a similar effect on the inductive reactance of the inductor when marker 140 is at two different positions that are about 180° apart from each other (e.g., the 6 o'clock and 12 o'clock positions if the outer perimeter of base 132 represents the outer perimeter of a clock) and equidistant from the inductor. As a result, the inductive reactance of the inductor in this case would indicate marker 140 is at one of two possible rotational positions. On the other hand, with two inductors unevenly distributed (e.g., less than 180 degrees apart, such as at about the 4 o'clock position and the 8 o'clock position) around base 132, ferromagnetic marker 140 can be at two different positions about 180 degrees apart from each other and result in different inductive reactances of the inductors, thereby making the position of the marker 140 distinguishable.

A burr hole cap assembly that includes three or more inductors with respective circuits may enable a triangulation solution for determining the position of ferromagnetic marker 140. While three, four or more inductors may be redundant in some cases, the use of four or more inductors to determine the rotational position of marker 40 relative to base 132 may be useful in increasing accuracy of the rotational position determination, such as by enabling a higher resolution of rotational position determination. In addition, the use of four or more inductors may also be useful fir detecting a smaller ferromagnetic marker. As discussed above, the configuration of ferromagnetic marker 140, including the size, may affect how it affects the inductive reactances of inductors 134, 136 of base 132.

In some cases, other ferromagnetic or electromagnetic elements of the environment may interfere with the inductive reactance of a reactive element. The use of more than two inductors can also enable processor 144 to minimize the possibility of inaccurately determining the rotational position of marker 140 relative to base 132, e.g., by comparing the position determined based on different sets of reactive elements and/or validating one position determined based on one or more reactive elements with another position determined based on different one or more reactive elements.

In other examples, base 132 may include one inductor, two inductors, or more than two inductors, and the rotational orientation of ferromagnetic marker 140 of rotatable member 133 relative to base 132 may be determined based on the inductive reactance of the one inductor or the more than two inductors.

Figure 14:
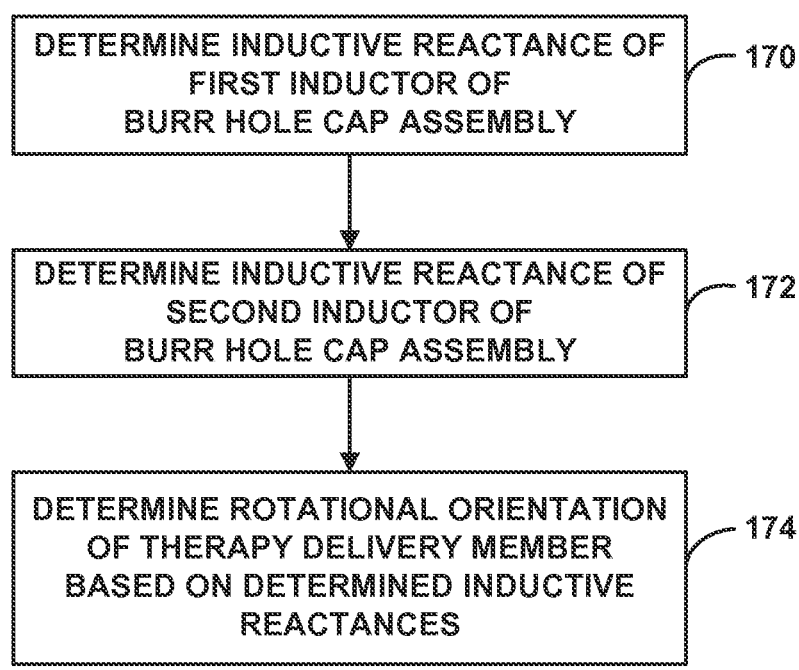
FIG. 14 is a flow diagram of an example technique for determining a rotational orientation of a therapy delivery member relative to the burr hole cap assembly shown in FIG. 12.

FIG. 14 is a flow diagram of an example technique for determining a rotational orientation of therapy delivery member 12 relative to base 132 of burr hole cap assembly 130. The technique shown in FIG. 14 may be implemented, for example, after therapy delivery member 12 is implanted in patient 14, and after burr hole cap assembly 130 is covered, e.g., by the patient's scalp. Thus, burr hole cap assembly 130 may be an elegant way of determining the rotational orientation of therapy delivery member 12 relative to base 132 of burr hole cap assembly 130 even after burr hole cap assembly 130 is not relatively easily accessible. Although the technique shown in FIG. 14 is described with respect to burr hole cap assembly 130, in other examples, other burr hole cap assemblies with one or more inductors may be used in a similar manner to determine a rotational orientation of therapy delivery member 12 relative to base 132 of burr hole cap assembly 130 after therapy delivery member 12 is implanted in patient 14, and after burr hole cap assembly 130 is covered, e.g., by the patient's scalp.

In accordance with the technique shown in FIG. 14, the inductive reactance of a first inductor 134 of burr hole cap assembly 130 is determined (170). In some examples, a user may utilize reader device 142 to interrogate inductor 134 to determine the inductive reactance of inductor 134. The user may place reader device 142 near burr hole cap assembly 130 (e.g., adjacent the patient's scalp near burr hole cap assembly 130). As discussed above, coil 148 of reader device 142 may generate a magnetic field that energizes inductor 134. When inductor 134 is energized, sensor 150 may sense one or more properties of the magnetic field generated by inductor 134, where the properties are indicative of the inductive reactance of inductor 134. Processor 144 of reader device 142 or another device (e.g., a medical device programmer, a computing device utilized by a clinician or the like) may then determine the inductive reactance of inductor 134 based on the one or more sensed properties of the magnetic field generated by inductor 134 in response to the energization. The inductive reactance of a second inductor 136 of burr hole cap assembly 130 can be determined (172), e.g., in a similar manner as that discussed above with respect to inductor 134.

The inductive reactance of each of the inductors 134, 136 may be determined at separate times in some examples, or at the same time in other examples. After determining the inductive reactances of the inductors 134, 136, the rotational orientation of therapy delivery member 12 relative to base 132 can be determined based on the determined inductive reactances (174). In one example, processor 144 of reader device 142 determines a ratio of the distance between ferromagnetic marker 140 of rotatable member 133 and inductor 134 to the distance between ferromagnetic marker 140 and inductor 136 and determines the rotational orientation of marker 140 relative to base 132 associated with the determined ratio in memory 146 of reader device 142.

In another example, processor 144 determines the absolute values of the inductive reactances of inductors 134, 136, which may in some cases indicate the rotational position of marker 140 better than the ratio of inductive reactances. For example, when marker 140 is positioned equidistant from both inductors 134, 136 (e.g., when marker 140 is at either the 6 o'clock or 12 o'clock position when inductors 134, 136 are at the 4 o'clock and 8 o'clock positions, respectively), the ratio of the inductive reactances may not indicate which of these two rotational positions marker 140 is positioned, whereas marker 140 at the equidistant position that is closer to inductors 134, 136 (e.g., the 6 o'clock position versus the 12 o'clock position) may have a larger impact on the inductive reactances of inductors 134, 136 than the other equidistant position. In this way, the absolute inductive reactance values of the inductors 134, 136 may be used to determine the rotational position of marker 140 in some examples. Because marker 140 is substantially aligned with marker 36 of therapy delivery member 12, the determined rotational orientation of ferromagnetic marker 140 relative to base 132 may be substantially the same, or at least indicative of the rotational orientation of therapy delivery member 12 relative to base 132.

In other examples, burr hole cap assembly 130 (e.g., base 132 or a cap) may have radiopaque elements that allow its orientation and location to be registered to anatomical images of patient 14. The rotational position of ferromagnetic marker 140 (or a visible marker in a fixed position relative to ferromagnetic marker 140) can then be used to find the rotational orientation of therapy delivery member 12 relative to the brain of patient 14.

As discussed above, base 132 may be implanted in a known orientation relative to brain of patient 14, such that the position of inductors 134, 136 relative to one or more target brain structures may be determined. As a result, once the rotational orientation of marker 140 relative to base 132 is determined, the orientation of one or more therapy delivery elements of therapy delivery member 12 relative to one or more target brain structures of patient 14 may be determined.

In other examples, other mechanisms can be used to change the inductance of one or more inductors of a burr hole cap assembly such that the inductance is indicative of the rotational orientation of a therapy delivery member relative to the burr hole cap assembly. In the example discussed with respect to FIGS. 12 and 13, an element of rotatable member 133 is implemented to change the response of the inductors 134, 136. In other examples, a geometry of an inductor of a burr hole cap assembly may be configured to change (directly in some examples or indirectly in others) as a function of the rotational orientation of a therapy delivery member relative to the burr hole cap assembly, where the geometry affects the inductance of the inductor. Thus, the inductance of the inductor may indicate the rotational orientation of a therapy delivery member relative to the burr hole cap assembly.

As an example, in one example, an inductor of the burr hole cap assembly may have an adjustable core that is configured to move relative to a coiled conductor of the inductor. As the core moves different distances in and out of the coil (e.g., the core may fit within the space defined by the inner perimeter of the coil), the inductance of the inductor may change. The core of the inductor may be configured such that the relative position of the core and the coiled conductor is indicative of the rotational orientation of a therapy delivery member relative to the burr hole cap assembly. Accordingly, the inductance of the inductor may change as a function of the rotational orientation of a therapy delivery member relative to the burr hole cap assembly.

For example, a burr hole cap assembly may include a rotatable member (e.g., similar to rotatable member 114 shown in FIG. 10) that is configured to rotate relative to abuse, and the rotatable member may be configured such that as it rotates relative to the base, the adjustable core moves relative in or out of the coil defined by the coiled conductor of the inductor, depending on which way the rotatable member is rotated. The movement of the adjustable core relative to the coiled conductor may be proportional to the movement of the rotatable member relative to the base in some examples. The inductor can be mechanically coupled to the base in some examples, and may only be mechanically connected to the rotatable member in other examples.

The rotatable member may include a first marker that is in a fixed position on the rotatable member. After a therapy delivery member is introduced through an opening defined by the base of the burr hole cap assembly, a clinician can rotate the member to substantially align the first marker with marker 36 on therapy delivery member 12, e.g., as described above with respect to rotatable member 114 shown in FIG. 10. Thus, the clinician can manipulate the first marker until it is indicative of the rotational orientation of therapy delivery member 12. The marker on the therapy delivery member need not be ferromagnetic in this example. Due to the mechanical coupling between the adjustable core of the inductor and the rotatable member of the burr hole cap assembly movement of the rotatable member to align the marker on the rotatable member with marker 36 on therapy delivery member 12 incidentally moves the core of the inductor relative to the coiled conductor. Accordingly, after therapy delivery member 12 is implanted patient 14 and is no longer visible without the aid of medical imaging, the rotational orientation of therapy delivery member 12 can be determined by interrogating the inductor (e.g., with reader device 142 shown in FIG. 12) to determine its inductance.

The inductance of the inductor is indicative of the position of the core relative to the coiled conductor, which is indicative of the rotational orientation of the first marker of the rotatable member. As discussed above, the first marker can be substantially aligned with marker 36 of therapy delivery member 12, such that the position of the first marker of the rotatable member is indicative of the position of marker 36. Because the orientation of the burr hole base relative to the patient's cranium 18 and the position of marker 36 relative to therapy delivery elements of member 12 are known, the rotational orientation of the therapy delivery elements relative to the cranium 18 may be determined based on the inductance of the inductor.

In some examples, a device (e.g., reader device 142, another external computing device, or an implanted device) can store a plurality of inductance values of the inductor and associate the inductance values with different rotational positions of the first marker. These rotational positions may be indicated with respect to, for example, a known anatomical landmark (e.g., the 0° rotational position may be substantially aligned with the patient's nose) when the base of the burr hole cap assembly is implanted in a known orientation relative to the anatomical landmark. Thus, in some examples, a processor and/or clinician can determine the rotational orientation of therapy delivery member 12 in a brain of patient 14 by determining the inductance of an inductor of the burr hole cap assembly, and determining the rotational position associated with the inductance. Moreover, in this example, the burr hole cap assembly is configured to transmit an indication (e.g., an inductance) that is indicative of the rotational orientation of a therapy delivery member relative to the burr hole cap assembly.

In another example of a burr hole cap assembly that comprises an inductor with a geometry that is configured to change as a function of the rotational orientation of a therapy delivery member relative to the burr hole cap assembly, a burr hole cap assembly may comprise a rotatable member (e.g., similar to rotatable member 114 shown in FIG. 10) that is configured to rotate relative to a base, and the rotatable member may be configured such that as it rotates relative to the base, the portion of the conductor of the inductor that is coiled changes, e.g., the length of the coiled conductor increases or decreases depending on which way the rotatable member is rotated. For example, the ends of the conductor may be mechanically connected to the rotatable member, such that the rotational orientation of the rotatable member relative to the base changes the position of the ends of the conductor relative to, e.g., the center axis of the coil defined by the conductor. Again, the inductor can be mechanically coupled to the base in some examples, and may only be mechanically connected to the rotatable member in other examples.

The increase or decrease in the length of the coiled conductor may be proportional to the movement of the rotatable member relative to the base in some examples. As described in further detail below, the rotatable member may be rotated to a position to indicate the rotational orientation of therapy delivery member 12 relative to the burr hole cap assembly; such that the length of the coiled conductor is also indicative of the rotational orientation of therapy delivery member 12 relative to the burr hole cap assembly. Because the length of the coiled conductor may affect the inductance of the inductor, the inductance of the inductor may change as a function of the rotational orientation of therapy delivery member 12 relative to the burr hole cap assembly.

As with the previously described example, in this example, the rotatable member may include a first marker that is in a fixed position on the rotatable member. After therapy delivery member 12 is introduced through an opening defined by the base of the burr hole cap assembly, a clinician can rotate the member to align the first marker with marker 36 on the therapy delivery member, e.g., as described above with respect to rotatable member 114 shown in FIG. 10. Marker 36 on therapy delivery member 12 need not be ferromagnetic in this example. Due to the mechanical coupling between the coiled conductor and the rotatable member of the burr hole cap assembly, movement of the rotatable member to align the marker on the rotatable member with marker 36 on therapy delivery member 12 incidentally changes the length of the coiled portion of the conductor. Accordingly, after therapy delivery member 12 is implanted in patient 14 and is no longer visible without the aid of medical imaging, the rotational orientation of therapy delivery member 12 can be determined by interrogating the inductor (e.g., with reader device 142 shown in FIG. 12) to determine its inductance.

The inductance of the inductor is indicative of the length of the coiled portion of the conductor, which is indicative of the rotational orientation of the first marker of the rotatable member. Because the position of the first marker of the rotatable member is indicative of the position of marker 36 of therapy delivery member 12 and the orientation of the base of the burr hole cap assembly relative to the patient's cranium 18 is known, the rotational orientation of therapy delivery member 12 relative to the patient's cranium 18 may be determined based on the inductance of the inductor.

As with the previous example, in some examples, a device (e.g., reader device 142, another external computing device, or an implanted device) can store a plurality of inductance values of the inductor and associate the inductance values with different rotational positions of the first marker. Thus, in some examples, a processor and/or clinician can determine the rotational orientation of therapy delivery member 12 in a brain of a patient by determining the inductance of an inductor of the burr hole cap assembly, and determining the rotational position associated with the inductance. In this example, the burr hole cap assembly is configured to transmit an indication (e.g., an inductance) that is indicative of the rotational orientation of a therapy delivery member relative to the burr hole cap assembly.

In another example, a burr hole cap assembly can include a capacitive element that has a configuration, and, therefore, capacitance, that changes as a function of the rotational orientation of a therapy delivery member relative to the burr hole cap assembly. The capacitive element can include a dielectric between capacitor plates. In this example, a burr hole cap assembly may comprise a rotatable member (e.g., similar to rotatable member 114 shown in FIG. 10) that is configured to rotate relative to a base, and the rotatable member may be configured such that as it rotates relative to the base, the dielectric and plates move relative to each other. For example, the dielectric portion of the capacitive element may be mechanically connected to the rotatable member such that the dielectric portion moves relative to two plates as the rotatable member is rotated relative to the base. As another example, the plates of the capacitive element may be mechanically connected to the rotatable member and may, e.g., move closer together or further apart from each and other and relative to the dielectric, depending on the direction in which the rotatable member is rotated.

In either case, the movement of the dielectric or plates may be proportional to the movement of the rotatable member relative to the base. When the clinician rotates the rotatable member to a position to indicate the rotational orientation of therapy delivery member 12 relative to the burr hole cap assembly, the capacitance of the capacitive element changes due to the change in the position of the dielectric or plates. As a result, the capacitance of the capacitive element may uniquely indicate the rotational orientation of a marker on the rotatable member (which may be aligned with marker 36 on therapy delivery member 12). Accordingly, after therapy delivery member 12 is implanted in patient 114 and is no longer visible without the aid of medical imaging, the rotational orientation of therapy delivery member 12 can be determined by interrogating the capacitive element (e.g., with reader device 142 shown in FIG. 12) to determine its capacitance. A device (e.g., reader device 142, another external computing device, or an implanted device) can store a plurality of capacitance values of the capacitive element and associate parameters indicative of the capacitance (e.g., capacitance values) with different rotational positions of the marker on the rotatable member.

In examples in which a device, such as reader device 142, determines a rotational orientation of therapy delivery member 12 relative to a burr hole cap assembly, the device may be configured to communicate this information (e.g., via a wired or wireless communication technique) to other components (e.g., an implantable medical device or medical device programmer) for further programming and decision making.

While FIGS. 12 and 13 describe examples in which a burr hole cap assembly includes at least one inductor whose inductance can be indicative of a rotational orientation of a therapy delivery member, in other examples, a burr hole cap assembly can include one or more other types of reactive elements in addition to or instead of the reactive elements including an inductor, capacitive element, or both, where the impedance (or capacitance) of the one or more reactive elements is indicative of the rotational orientation of the therapy delivery member relative to the burr hole cap.

The techniques described in this disclosure, including those attributed to reader device 142, computing devices, or various constituent components, may be implemented, at least in part, in hardware, software, firmware or any combination thereof. For example, various aspects of the techniques may be implemented within one or more processors, including one or more microprocessors, DSPs, ASICs, FPGAs, or any other equivalent integrated or discrete logic circuitry, as well as any combinations of such components, embodied in programmers, such as physician or patient programmers, stimulators, image processing devices or other devices. The term "processor" or "processing circuitry" may generally refer to any of the foregoing logic circuitry, alone or in combination with other logic circuitry, or any other equivalent circuitry.

Such hardware, software, and/or firmware may be implemented within the same device or within separate devices to support the various operations and functions described in this disclosure. Thus, techniques described herein are primarily described as being performed by a specific processor, any one or more parts of the techniques described herein may be implemented by a processor of any suitable computing device, alone or in combination with each other. In addition, any of the described units, modules or components may be implemented together or separately as discrete but interoperable logic devices. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components.

When implemented in software, the functionality ascribed to the systems, devices and techniques described in this disclosure may be embodied as instructions on a computer-readable medium such as RAM, ROM, NVRAM, EEPROM, FLASH memory, magnetic data storage media, optical data storage media, or the like. The instructions may be executed to support one or more aspects of the functionality described in this disclosure.

Various examples have been described. These and other examples are within the scope of the following claims.

What is claimed is:

1. A system comprising:
   a therapy delivery member configured to deliver therapy from a medical device to a patient;
   a base that is configured to be positioned at least partially inside of a burr hole in a cranium of a patient, wherein the base defines an opening, and wherein the therapy delivery member is configured to be introduced through the opening into the burr hole in the cranium of the patient when the base is positioned at least partially inside of the burr hole;
   a marker that is configured to indicate a rotational orientation of the therapy delivery member about a longitudinal axis of the therapy delivery member within the opening relative to the base; and a cover that is configured to substantially cover the opening defined by the base when the therapy delivery member extends through the opening, wherein the base, the marker, and the cover are configured to be implanted under a skin of the patient while the base is positioned at least partially inside of the burr hole in the cranium of the patient, the therapy delivery member extends through the opening into the burr hole in the cranium of the patient, and the cover substantially covers the opening defined by the base.

2. The system of claim 1, wherein the cover is configured to substantially fix a position of the therapy delivery member relative to the base when the therapy delivery member extends through the opening defined by the base.

3. The system of claim 1, wherein the marker comprises a visible marker positioned on the base.

4. The system of claim 1, wherein the marker comprises a radiopaque marker.

5. The system of claim 1, wherein the system comprises a plurality of individual markers, the plurality of individual markers including the marker, and wherein the plurality of individual markers indicate respective positions around the base.

6. The system of claim 1, further comprising a rotatable member that is configured to rotate relative to the base, wherein the rotatable member comprises the marker.

7. The system of claim 1, wherein the marker comprises an indicator element that is configured to be located in the cranium of the patient or around the base at a position that indicates the rotational orientation of the therapy delivery member about the longitudinal axis of the therapy delivery member within the opening relative to the base, and wherein the indicator element is movable relative to the base and the cover.

8. The system of claim 7, wherein the indicator element is radiopaque.

9. The system of claim 1, further comprising an inductor, wherein at least one of an inductive reactance or an inductance of the inductor is indicative of a rotational orientation of the marker relative to the base.

10. The system of claim 9, further comprising a reader device that is configured to determine a parameter indicative of the inductive reactance of the inductor.

11. The system of claim 9, further comprising a rotatable member that comprises the marker and the inductor, the rotatable member being rotatable relative to the base, wherein the at least one of the inductive reactance or the inductance of the inductor changes based on a rotational position of the rotatable member relative to the base.

12. The system of claim 11, wherein the inductor comprises a conductive coil and a core movable relative to the conductive coil, and wherein the rotatable member is mechanically connected to the core and configured such that rotation of the rotatable member relative to the base moves the core relative to the conductive coil.

13. The system of claim 11, wherein the inductor comprises a conductive coil mechanically connected to the rotatable member, and wherein rotation of the rotatable member relative to the base changes a coiled length of the conductive coil.

14. The system of claim 1, further comprising:
a capacitive element; and
a rotatable member that comprises the marker and the capacitive element, the rotatable member being rotatable relative to the base, wherein a capacitance of the capacitive element changes based on a rotational position of the rotatable member relative to the base.

15. The system of claim 1, wherein the marker comprises a ferromagnetic material, the system further comprising:
an inductor within the base; and
a rotatable member that comprises the marker, the rotatable member being rotatable relative to the base, wherein the inductance of the inductor changes based on a rotational position of the marker relative to the base.

16. The system of claim 1, wherein the marker comprises a first marker, wherein the therapy delivery member includes a second marker, the first marker being configured to be moved relative to the base to substantially align with the second marker.

17. The system of claim 1, further comprising an inductor within the base, wherein the therapy delivery member comprises the marker, the marker comprising a ferromagnetic marker, and wherein a proximity of the ferromagnetic marker to the inductor indicates the rotational orientation of the therapy delivery member relative to the base.

18. A method comprising
introducing a therapy delivery member through an opening defined by a base of a burr hole cap assembly into a burr hole in a cranium of a patient, wherein the therapy delivery member is configured to deliver therapy from a medical device to the patient, wherein the base is configured to be positioned at least partially inside of the burr hole in the cranium of the patient, wherein the burr hole cap assembly includes a marker that is configured to indicate a rotational orientation of the therapy delivery member about a longitudinal axis of the therapy delivery member within the opening relative to the base and a cover that is configured to substantially cover the opening defined by the base when the therapy delivery member extends through the opening;
indicating the rotational orientation of the therapy delivery member about the longitudinal axis of the therapy delivery member relative to the base with the marker of the burr hole cap assembly; and
implanting the base, the marker, and the cover such that base, the marker, and the cover are under a skin of the patient while the base is positioned at least partially inside of the burr hole in the cranium of the patient, the therapy delivery member extends through the opening into the burr hole in the cranium of the patient, and the cover substantially covers the opening defined by the base.

19. The method of claim 18, wherein the marker comprises a first marker, and indicating the rotational orientation of the therapy delivery member about the longitudinal axis of the therapy delivery member relative to the base comprises:
locating a second marker on the therapy delivery member; and
locating, from among a plurality of markers that are at different positions around a perimeter of the base, the first marker that substantially aligns with a second marker.

20. The method of claim 18, wherein the marker comprises a first marker and the therapy delivery member comprises a second marker, and wherein indicating the rotational orientation of the therapy delivery member about the longitudinal axis of the therapy delivery member relative to the base comprises rotating a rotatable member that comprises the first marker to substantially align the first marker with the second marker, wherein the rotatable member is rotatable relative to the base.

21. The method of claim 20, wherein the rotatable member comprises an inductor, wherein at least one of an inductive reactance or an inductance of the inductor is indicative of a rotational orientation of the first marker about the longitudinal axis of the therapy delivery member relative to the base, the method further comprising, after introducing the therapy delivery member through the opening defined by the base, determining the rotational orientation of the therapy delivery member about the longitudinal axis of the therapy delivery member relative to the base by at least determining a parameter indicative of the at least one of the inductive reactance or the inductance of the inductor.

22. The method of claim 21, wherein the inductor comprises a conductive coil and a core movable relative to the conductive coil, and wherein the rotatable member is mechanically connected to the core and configured such that rotation of the rotatable member relative to the base moves the core relative to the conductive coil.

23. The method of claim 21, wherein the inductor comprises a conductive coil mechanically connected to the rotatable member, and wherein rotation of the rotatable member relative to the base changes a coiled length of the conductive coil.

24. The method of claim 20, wherein the rotatable member comprises a capacitive element, wherein a capacitance of the capacitive element changes based on a rotational position of the rotatable member relative to the base, the method further comprising, after introducing the therapy delivery member through the opening defined by the base, determining the rotational orientation of the therapy delivery member about the longitudinal axis of the therapy delivery member relative to the base by at least determining a parameter indicative of the capacitance of the capacitive element.

25. A system comprising:
means for delivering therapy from a medical device to a patient;
means for covering a burr hole in a cranium of a patient, wherein the means for covering the burr hole defines an opening, wherein the means for delivering therapy is configured to be introduced through the opening into the burr hole in the cranium of the patient when the means for covering the burr hole is positioned at least partially inside of the burr hole; and
means for indicating a rotational orientation of the means for delivering therapy about a longitudinal axis of the means for delivering therapy within the opening relative to the means for covering the burr hole, wherein the means for covering the burr hole and the means for indicating the rotational orientation are configured to be implanted under a skin of the patient while the means for covering the burr hole is positioned at least partially inside of the burr hole.

26. The system of claim 25, wherein the means for indicating a rotational orientation of the means for delivering therapy about the longitudinal axis of the means for delivering therapy within the opening relative to the means for covering the burr hole comprises an reactive element, wherein a characteristic of the reactive element changes based on a rotational position of a first marker of the means for covering the burr hole, wherein the first marker is configured to be substantially aligned with a second marker of the means for delivering therapy.

27. The system of claim 25, wherein the means for indicating the rotational orientation of the means for delivering therapy within the opening relative to the means for covering the burr hole is visible and at least partially radiopaque.

28. The system of claim 1, wherein marker comprises a first marker located at a position on an outer surface of the therapy delivery member.

29. The system of claim 28, wherein the therapy delivery member includes at least one of a fluid delivery port or electrode located distally from the first marker on the therapy delivery member, wherein the position of the first marker on the outer surface of the therapy member is indicative of a circumferential position of the at least one of a fluid delivery port or electrode on the therapy delivery member.

30. The system of claim 28, wherein the marker includes a second marker located on the base, wherein the orientation of the first marker relative to the second marker is configured to indicate an orientation of the therapy delivery member within the opening relative the base.

31. The system of claim 1, wherein the therapy delivery member includes an implantable electrical lead including at least one electrode, wherein the therapy includes at least one of delivery of electrical stimulation from the medical device to the patient via the at least one electrode or sensing of bioelectrical brain signals of the patient via the at least one electrode.

32. The system of claim 1, wherein the therapy delivery member includes a fluid delivery conduit that terminates a fluid delivery port, wherein the therapy includes the delivery of a fluid from the medical device to the patient via the fluid delivery port.

33. The system of claim 1, wherein the marker comprises an alphanumeric indicator at a perimeter of the opening.

34. The system of claim 33, wherein the alphanumeric indicator is indicative of a unit of measurement at the perimeter of the opening.

35. The system of claim 1, further comprising the medical device.

36. The system of claim 25, further comprising the medical device.

* * * * *